US010139419B2

United States Patent
Cliff et al.

(10) Patent No.: US 10,139,419 B2
(45) Date of Patent: Nov. 27, 2018

(54) METHODS FOR DETECTING Aβ OLIGOMERS

(71) Applicant: SYSTEM OF SYSTEMS ANALYTICS, INC., Fairfax, VA (US)

(72) Inventors: Richard O. Cliff, Fairfax, VA (US); Robert W. Flower, Fairfax, VA (US); Evgenia G. Matveeva, Fairfax, VA (US)

(73) Assignee: SYSTEM OF SYSTEMS ANALYTICS, INC., Fairfax, VA (US)

( * ) Notice: Subject to any disclaimer, the term of this patent is extended or adjusted under 35 U.S.C. 154(b) by 224 days.

(21) Appl. No.: 14/845,731

(22) Filed: Sep. 4, 2015

(65) Prior Publication Data

US 2016/0169913 A1     Jun. 16, 2016

Related U.S. Application Data

(60) Provisional application No. 62/046,475, filed on Sep. 5, 2014.

(51) Int. Cl.
| | |
|---|---|
| *G01N 33/537* | (2006.01) |
| *G01N 33/68* | (2006.01) |
| *G01N 33/49* | (2006.01) |
| *G01N 33/58* | (2006.01) |

(52) U.S. Cl.
CPC ....... *G01N 33/6896* (2013.01); *G01N 33/491* (2013.01); *G01N 33/4915* (2013.01); *G01N 33/537* (2013.01); *G01N 33/582* (2013.01); *G01N 2333/4709* (2013.01); *G01N 2800/2821* (2013.01)

(58) Field of Classification Search
CPC ............. G01N 33/6896; G01N 33/537; G01N 33/582; G01N 33/491; G01N 33/4915; G01N 2333/4709; G01N 2800/2821
See application file for complete search history.

(56) References Cited

U.S. PATENT DOCUMENTS

| 5,976,817 | A | 11/1999 | Davies-Heerema et al. |
| 8,673,579 | B2 | 3/2014 | Orser et al. |
| 2006/0205024 | A1 | 9/2006 | Rogers et al. |
| 2010/0129847 | A1* | 5/2010 | Navarrete Santos ......... G01N 33/542 435/29 |
| 2011/0092445 | A1* | 4/2011 | Barghorn ........... C07K 14/4711 514/21.1 |
| 2013/0295095 | A1 | 11/2013 | Bayer et al. |

FOREIGN PATENT DOCUMENTS

| EP | 1 882 944 A1 | 1/2008 |
| WO | WO-2011/056958 A2 | 5/2011 |
| WO | WO-2012/149145 A2 | 11/2012 |

OTHER PUBLICATIONS

Pesini et al. Reliable Measurements of the B-amyloid Pool in Blood Could Help in the Early Diagnosis of AD. International Journal of Alzheimer's Disease. vol. 2012, Article ID 604141 (May 2012).*
Neumann et al. Human Platelet Tau: A Potential Peripheral Marker for Alzheimer's Disease. Journal of Alzheimer's Disease 25: 103-109 (2011).*
Nakagawa et al. Amyloid B-induced erythrocytic damage and its attenuation by carotenoids. FEBS 585: 1249-1254 (2011).*
Kiko et al., "Amyloid β Levels in Human Red Blood Cells," PLoS One, vol. 7, Issue 11, pp. 1-6, Nov. 15, 2012.
International Search Report dated Feb. 12, 2016 in application No. PCT/US2015/048504.
Santos et al., "Amyloid-β Oligomers in Cerebrospinal Fluid are Associated with Cognitive Decline in Patients with Alzheimer's Disease," Journal of Alzheimer's Disease, vol. 29, pp. 171-176, 2012.
Santos et al., "A Method for the Detection of Amyloid-$\beta_{1-40}$, Amyloid-$\beta_{1-42}$ and Amyloid-β Oligomers in Blood Using Magnetic Beads in Combination with Flow Cytometry and its Application in the Diagnostics of Alzheimer's Disease," Journal of Alzheimer's Disease, vol. 14, pp. 127-131, 2008.
Santos et al., "Detection of Amyloid-β Oligomers in Human Cerebrospinal Fluid by Flow Cytometry and Fluorescence Resonance Energy Transfer," Journal of Alzheimer's Disease, vol. 11, pp. 117-125, 2007.
Broersen et al., "The culprit behind amyloid beta peptide related neurotoxicity in Alzheimer's disease: oligomer size or conformajtion?," Alzheimer's Research & Therapy, vol. 2, No. 12, pp. 1-14, Feb. 2012.
Nakagawa et al., "Amyloid β-induced erythrocytic damage and its attenuation by carotenoids," FEBS Letters, vol. 585, pp. 1249-1254, 2011.
Nakagawa et al., "Amyloid β Induces Adhesion of Erythrocytes to Endothelial Cells and Affects Endothelial Viability and Functionality," Biosci. Biotechnol. Biochem., vol. 75, No. 10, pp. 2030-2033, 2011.
Nicolay et al., "Amyloid Induced Suicidal Erythrocyte Death," Cellular Physiology and Biochemistry, vol. 19, pp. 175-184, 2007.
O'Bryant et al., "A Blood-Based Screening Tool for Alzheimer's Disease That Spans Serum and Plasma: Findings from TARC and ADNI," PLoS One, vol. 6, No. 12, pp. 1-8, Dec. 2011.
Villemagne et al., "Blood-Borne Amyloid-β Dimer Correlates with Clinical Markers of Alzheimer's Disease," The Journal of Neuroscience, vol. 30, No. 18, pp. 6315-6322, May 5, 2010.
Fletcher et al., "Diagnosing Alzheimer's disease: are we any nearer to useful biomarker-based, non-invasive tests:," GMC Health Technol. Assess., vol. 9, Document 01, Nov. 2013.
Handoko et al., "Correlation of Specific Amyloid-β Oligomers with Tau in Cerebrospinal Fluid From Cognitively Normal Older Adults," JAMA Neurol., vol. 70, No. 5, pp. 594-599, Mar. 2013.

(Continued)

*Primary Examiner* — Gailene Gabel
(74) *Attorney, Agent, or Firm* — Foley & Lardner LLP

(57) ABSTRACT

Methods of detecting Aβ oligomers, such as may be present in a biological sample are described. The methods include detection using flow cytometry, detection using synthetic Aβ oligomers and/or in vitro methods detecting Aβ oligomers associated with cells.

14 Claims, 13 Drawing Sheets

Specification includes a Sequence Listing.

(56) References Cited

OTHER PUBLICATIONS

Koyama et al., "Plasma Amyloid-β as a Predictor of Demetia and Cognitive Decline," Arch. Neural., vol. 69, No. 7, pp. 824-831, Jul. 2012.
Roed et al., "Prediction of Mild Cognitive Impairment that Evolves into Alzheimer's Disease Dementia with Two Years using a Gene Expression Signature in Blood: A Pilot Study," Journal of Alzheimer's Disease, vol. 35, pp. 611-621, Feb. 2013.
Pesini et al., "Reliable Measurements of the β-Amyloid Pool in Blood Could Help in the Early Diagnosis of AD," International Journal of Alzheimer's Disease, vol. 2012, Article ID 604141, May 2012.
Emadi et al., "Detecting Morphologically Distinct Oligomeric Forms of α-Synuclein," Journal of Biological Chemistry, vol. 284, No. 17 (Apr. 2009), pp. 11048-11058.
Funke, "Detection of Soluble Amyloid-β Oligomers and Insoluble High-Molecular-Weight Particles in CSF: Development of Methods with Potential for Diagnosis and Therapy Monitoring of Alzheimer's Disease", International Journal of Alzheimer's Disease (Jan. 2011), vol. 2011, pp. 1-8.

\* cited by examiner

PLISA selectivity (compared to ELISA)

Table 1. Percentage of the spiked monomer and fiber signal (from ratio to the spiked oligomer signal) measured by PLISA versus ELISA (in buffer)*

| [oligomer], nN | monomer/oligomer signal in % | | fiber / oligomer signal in % | |
|---|---|---|---|---|
| | PLISA | ELISA | PLISA | ELISA |
| 150 | 19 | 80 | 12 | 37 |
| 50 | 6 | 70 | 12 | 40 |
| 16.7 | 11 | 60 | 22 | 41 |

* Peptide: AD-317; blocking buffer TBST (TBS containing 0.05% Tween-20); buffer (20 mM Hepes, pH 7.0, containing 0.05% NP-40 and 1% fish gelatin) spiked with oligomer, or monomer, or fiber.

Table 2. Percentage of the spiked monomer signal (from ratio to the spiked oligomer signal) measured by PLISA versus ELISA (in 10% CSF)**

| [oligomer], nN | monomer/oligomer signal in % | |
|---|---|---|
| | PLISA | ELISA |
| 30 | 17 | 112 |
| 6 | 14 | 111 |
| 1.2 | N/A | 113 |

** Peptide: AD-317; blocking buffer TBST (TBS containing 0.05% Tween-20); CSF/buffer – mix of 10% CSF and 90% buffer (20 mM Hepes, pH 7.0, containing 0.05% NP-40 and 10% Superblock) spiked with oligomer, or monomer.

FIGURE 9

Pep11 recognizes Oligomer from Fiber

Categorization of Clinical CSF samples based on MMSE, CDR, and ASAD-cog cognitive testing scores

METHODS FOR DETECTING Aβ OLIGOMERS

CROSS REFERENCE TO RELATED APPLICATIONS

This application claims the benefits of priority to U.S. Provisional Application No. 62/046,475, filed Sep. 5, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Oct. 9, 2015, is named 070538-0250_SL.txt and is 20,777 bytes in size.

BACKGROUND

The pathogenesis of misfolded protein disorders is characterized by the conversion of normal proteins into aggregation-prone β-sheet rich conformations. These conformations are implicated in amyloidogenic disease. In the case of Alzheimer's Disease (AD), self-assembly of amyloid beta (Aβ) protein into neurotoxic oligomers and fibrils is a leading postulation in regard to a major mechanism that causes AD.

Alzheimer's diseases is associated with a specific structural form of the Aβ protein (e.g., a "misfolded protein" or a self-aggregated protein), while the protein in a different structural form (e.g., a "normal protein") is not harmful. Misfolded Aβ protein form aggregates that self-assemble into non-branching fibrils with the common characteristic of a β-pleated sheet conformation. In the central nervous system (CNS), amyloid deposits can be present in cerebral and meningeal blood vessels (cerebrovascular deposits) and in brain parenchyma (plaques). Neuropathological studies in human and animal models indicate that cells proximal to amyloid deposits are disturbed in their normal functions. See, e.g., Mandybur, *Acta Neuropathol.* 78:329-331, 1989; Kawai et al., *Brain Res.* 623:142-146, 1993; Martin et al., *Am. J. Pathol.* 145:1348-1381, 1994; Kalaria et al., *Neuroreport* 6:477-80, 1995; Masliah et al., *J. Neurosci.* 16:5795-5811, 1996. Other studies additionally indicate that amyloid fibrils may actually initiate neurodegeneration. See, e.g., Lendon et al., *J. Am. Med. Assoc.* 277:825-831, 1997; Yankner, *Nat. Med.* 2:850-852, 1996; Selkoe, *J. Biol. Chem.* 271:18295-18298, 1996; Hardy, *Trends Neurosci.* 20:154-159, 1997.

While the underlying molecular mechanism that results in protein misfolding is still not completely understood, a common characteristic is the propensity to form aggregates and/or fibrils which exhibit a β-sheet structure or other conformations. Fibril formation and the subsequent formation of secondary β-sheet structures associated with plaque deposits, occurs via a complex mechanism involving a nucleation stage, in which monomers of the protein associate to form oligomers, which associate to form fibrils, followed by extension of the fibrils at each end. For example, Aβ protein monomers can be found in various parts of healthy individuals, including body fluids (e.g., blood and cerebrospinal fluid) and tissue (e.g., brain). Disease caused by misfolded Aβ protein appears to correlate with self-assembly of the monomers into oligomers (soluble aggregates), insoluble oligomers (e.g., insoluble amorphous self-aggregates), protofibrils, or fibrils, eventually forming into non-soluble, large aggregated deposits such as plaques found in diseased individuals.

Two abundant forms of Aβ protein found in amyloid plaques are $A\beta_{1-40}$ (also referred to as Aβ40) and $A\beta_{1-42}$ (also referred to as Aβ42). Although $A\beta_{1-40}$ is more abundant, Aβ42 is the more fibrillogenic and is the major component of the two in amyloid deposits of both AD and CAA. See, e.g., Wurth et al., *J. Mol. Biol.* 319: 1279-90 (2002). In addition to the amyloid deposits in AD cases described above, AD cases can be associated with amyloid deposition in the vascular walls. See, e.g., Vinters H. V., Stroke March-April; 18(2):311-324, 1987; Itoh Y., et al., *Neurosci. Lett.* 155(2):144-147, Jun. 11, 1993.

There is a need, therefore, for methods of detecting Aβ oligomers, which can provide insight into the risk for, presence, progression, severity and prognosis of disease and/or the efficacy of therapeutic agents aimed at disrupting the formation of Aβ protein aggregates.

SUMMARY

Disclosed herein are methods for detecting Aβ oligomers in a biological sample.

In accordance with some embodiments, the methods comprise detecting Aβ oligomers in a biological sample obtained from a subject, comprising preparing a test sample comprising the biological sample and a peptide probe, wherein the peptide probe consists of from 10 to 34 amino acid residues comprising an amino acid sequence that is at least 70% identical to any one of SEQ ID NOs:1-56 and 62-65, wherein the peptide probe preferentially binds to Aβ oligomers and is labeled with a fluorescent label capable of emitting a fluorescent signal, wherein the peptide probe forms complexes with any Aβ oligomer present in the biological sample; subjecting the test sample to flow cytometry to detect the fluorescent signal of the complexes; wherein the fluorescent signal of the complexes is directly correlated with the presence and amount of Aβ oligomers in the biological sample.

Also disclosed are methods comprising determining the Aβ oligomer load of a subject by detecting Aβ oligomer associated with cells present in a biological sample obtained from the subject, comprising: preparing a first test sample comprising a biological sample from the subject that comprises cells and a peptide probe, wherein the peptide probe consists of from 10 to 34 amino acid residues comprising an amino acid sequence that is at least 70% identical to any one of SEQ ID NOs:1-56 and 62-65, wherein the peptide probe preferentially binds to Aβ oligomers and is labeled with a detectable label, wherein the peptide probe forms a first complex with Aβ oligomer associated with cells in the biological sample; detecting a signal of the first complex in the first test sample; preparing a second test sample comprising a biological sample from the subject that comprises cells, synthetic Aβ oligomer, and the peptide probe, wherein the peptide probe forms second complexes with Aβ oligomer associated with cells in the biological sample and with synthetic Aβ oligomer; detecting a signal of the second complexes in the second test sample; wherein a difference between the signal of the first complex in the first test sample and the signal of the second complexes in the second test sample is inversely correlated with the Aβ oligomer load of the subject. In some embodiments, the second test sample is prepared by combining the biological sample and synthetic Aβ oligomer, and subsequently introducing the peptide probe.

Also disclosed are in vitro methods of detecting Aβ oligomer associated with erythrocytes, comprising contacting erythrocytes with a peptide probe, wherein the peptide probe consists of from 10 to 34 amino acid residues comprising an amino acid sequence that is at least 70% identical to any one of SEQ ID NOs:1-56 and 62-65, wherein the peptide probe preferentially binds to Aβ oligomers and is labeled with a detectable label, wherein the peptide probe forms a complex with Aβ oligomer associated with erythrocytes; detecting a signal of the complex.

Also disclosed are in vitro method of detecting Aβ oligomer associated with platelets, comprising contacting platelets with a peptide probe, wherein the peptide probe consists of from 10 to 34 amino acid residues comprising an amino acid sequence that is at least 70% identical to any one of SEQ ID NOs:1-56 and 62-65, wherein the peptide probe preferentially binds to Aβ oligomers and is labeled with a detectable label, wherein the peptide probe forms a complex with Aβ oligomer present on the surface of platelets; and detecting a signal of the complex.

In any of these methods, the detectable label may be a fluorescent label and the detecting steps may comprise subjecting the test samples to flow cytometry to detect a fluorescent signal of the complexes. In any of these methods, the fluorescent label may be an FITC label.

In any of these methods using a detectable label, the detectable label may be a fluorescent label and the detecting steps may comprise direct detection of the fluorescent signal of the complexes. In any of these methods using a detectable label, the detectable label may be a pyrene moiety and the detecting steps may comprise detecting pyrene excimer formation.

In any of these methods, the peptide probe may consist of SEQ ID NO:64 (Pep-11).

In any of these methods, the biological sample may comprise a sample of body fluid, such as blood, blood plasma, CSF, or brain homogenate. In any of these methods, the biological sample may comprise erythrocytes, including isolated erythrocytes. In any of these methods, the biological sample may comprise platelets, including isolated platelets. In some embodiments, the Aβ oligomer is associated with a cell, such as an erythrocyte and/or a platelet present in the biological sample. In some embodiments, the biological sample comprises erythrocytes and platelets and the methods comprise separately detecting Aβ oligomer associated with erythrocytes and Aβ oligomer associated with platelets.

In some embodiments, the complex formed and/or detected comprises peptide probe, Aβ oligomer, and an erythrocyte from the biological sample; peptide probe, Aβ oligomer, and a platelet from the biological sample; and/or peptide probe, synthetic Aβ oligomer, and an erythrocyte or platelet from the biological sample.

BRIEF DESCRIPTION OF THE DRAWINGS

FIG. 9 depicts the signal ratio (%) of Aβ monomer/oligomer and Aβ fiber/oligomer for different Aβ monomer, oligomer, and fiber concentrations in buffer and 10% cerebrospinalfluid (CSF) when probed with peptide probe as described herein, and demonstrates that peptide probes preferentially detect Aβ oligomer.

DETAILED DESCRIPTION

1. Definitions

Figure 1:
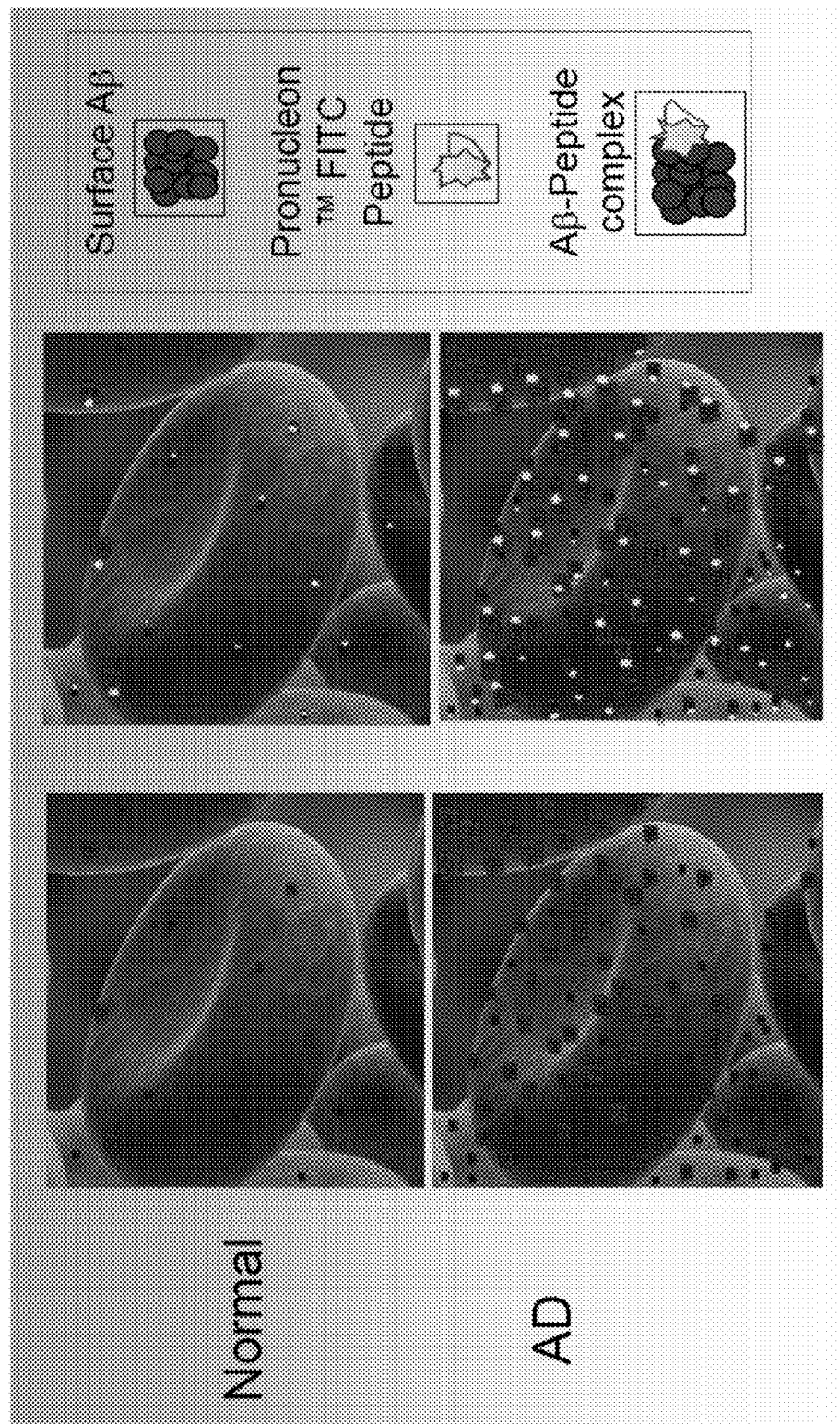
FIG. 1 depicts (i) endogenous Aβ oligomer associated with erythrocytes in whole blood samples from normal subjects or subjects with Alzheimer's Disease and (ii) complexes comprising labeled peptide probe and endogenous Aβ oligomer.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, "subject" denotes any animal including humans and domesticated animals, such as fish, cats, dogs, swine, cattle, sheep, goats, horses, rabbits, and the like. "Subject" also includes experimental, laboratory animal models, such as transgenic animals used in biology and medical research. "Subject" also includes animals used in research settings, including fish, worms, mice and other small mammals, including vertebrates and non-vertebrates. A typical subject may be suspected of suffering from amyloidogenic disease, suspected of having been exposed to conditions creating a risk for amyloidogenic disease, have a genetic risk for amyloidogenic disease (e.g., individuals with family members suffering from amyloidogenic disease or having ApoE4 allele variants), or may be desirous of determining risk or status with respect to amyloidogenic disease.

The term "biological sample" is used herein to refer to a sample from a subject. "Biological sample" includes body fluids, such as blood, cerebrospinal fluid, tissue homogenate, urine, saliva, serum, and sweat. "Blood" includes whole blood, blood cells (including erythrocytes, platelets, and leukocytes) and plasma. "Plasma" includes platelet-rich plasma and platelet-poor plasma. "Tissue homogenate" includes brain homogenate, other neural tissue homogenate, eye tissue homogenate, vascular tissue homogenate, lung tissue homogenate, kidney tissue homogenate, heart tissue homogenate, liver tissue homogenate and other tissue homogenates.

"Endogenous," "native," and "naturally occurring" oligomers refer to oligomers present in a source occurring in or obtained from nature, such as a biological sample from a subject. An endogenous oligomer may include post-translational modifications, including, but not limited to, acetylation, carboxylation, glycosylation, phosphorylation, lipidation, acylation, farnesylation and cleavage.

As used herein, "Aβ protein" includes $A\beta_{1-40}$ (also referred to as Aβ40) and $A\beta_{1-42}$ (also referred to as Aβ42), which represent alternative carboxy-terminal truncations of APP. See, e.g., Selkoe et al., PNAS USA 85:7341-7345, 1988; Selkoe, *Trends Neurosci.* 16:403-409, 1993. Aβ40 and Aβ42 have identical amino acid sequences, with Aβ42 having two additional residues (Ile and Ala) at its C terminus. The term also includes all naturally occurring mutants, including naturally occurring mutants known to exhibit increased tendency to form aggregates. Such mutants are known in the art, such as those disclosed in Murakami et al., *J. Biol. Chem.* 46:46179-46187, 2003, which is incorporated herein by reference in its entirety.

The term "Aβ oligomer" is used herein to refer to an association of two or more Aβ monomers. Monomers may be associated covalently or non-covalently, e.g., by covalent bonds, hydrogen bonds, ionic bonds, van der Waals interactions, etc. "Aβ oligomers" include, but are not limited to, for example, Aβ peptide dimers, trimers, tetramers, pentamers, hexamers, dodecamers, and higher order oligomers. An Aβ oligomer may comprise Aβ monomers having the same or different amino acid sequences. Typically, Aβ oligomers comprise Aβ proteins in the β-sheet conformation.

In some embodiments, the Aβ oligomer is a "soluble Aβ oligomer." As used herein, the term "soluble Aβ oligomer" means soluble in aqueous and/or physiological conditions at temperatures in the range of 25° C. to 37° C., such as about 25° C., about 30° C., about 35° C., and about 37° C. For example, a composition comprising a soluble Aβ oligomer would not have any particulate matter visible to the human eye and/or would not contain an appreciable amount of fibrillar particles as determined, for example, by ThT staining.

As used herein, "conformation" refers to the secondary or tertiary structure of a protein or peptide, for example, an alpha-helix, random coil or β-sheet secondary structure. A "conformation shift" means any change in the conformation of the non-primary structure of the protein, such as a change in the distance between the N- and C-termini (or between any other two points), folding more or less compactly, changing from predominantly one secondary structure to predominantly another secondary structure, such as from predominantly alpha helix/random coil to predominantly β-sheet, or any change in the relative amounts of different secondary structures, such as a change in the relative amounts of alpha helix/random coil and β-sheet secondary structures even without a change in the predominant secondary structure.

"Probe" refers to a peptide or peptide mimic that binds to Aβ oligomer. As used herein, a probe may or may not undergo a conformation shift upon association with Aβ oligomer. In some embodiments, the probe is a conformationally dynamic peptide based on the human Aβ protein sequence, as described in US 2010/0233095, the contents of which are incorporated herein by reference in their entirety. For convenience, the peptides and peptide mimics are referred to herein as "probes" without detracting from their utility in other contexts. These probes are discussed in more detail below.

"Peptide mimic" is also referred to as a peptidomimic or peptidomimetic or peptoid and refers to any molecule that mimics the properties of a peptide, such as peptide structure and certain physiochemical properties. Peptide mimics include polymeric molecules that mimic the folding and/or secondary structure of a specific peptide, as well as those that mimic the biological or chemical properties of a peptide. Peptide mimics may have an amino acid backbone and contain non-natural chemical or amino acid substitutions. Peptoids may have side chains (R-groups) on the backbone amide nitrogen, instead of the alpha carbon as in peptides. This may serve one or more of several purposes: (1) peptoids may be resistant to proteolysis; (2) since peptoid secondary structure formation may not depend on hydrogen bonding, they may exhibit enhanced thermal stability as compared to peptides, and (3) the large number of available peptoid residues allows for the production of a large variety of three-dimensional structures that may aid in assay development. Alternatively, peptide mimics may have different chemical backbones, such as β-peptides, anthranilamide oligomers, oligo (m-phenylene ethynylene), oligourea, oligopyrrolinones, azatides and N-substituted glycine oligomers. Peptide mimics may have different chemical properties, such as resistance to proteases, while retaining peptide characteristics, such as peptide folding and peptide-peptide interactions (including, for example, interactions via hydrogen bonding, etc.). Any suitable peptide mimic can be used in the present invention, and include those designed and/or constructed as described in Chongsiriwatana, N. P., et al.

Proc Natl Acad Sci USA 2008, 105, (8), 2794-9; Kirshenbaum, K., et al. *Current Opinion in Structural Biology* 1999, 9, (4), 530-535; Lee, B. C., et al., *Journal of the American Chemical Society* 2005, 127, (31), 10999-11009, which are each hereby incorporated by reference in their entirety.

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., *The Atlas of Protein Sequence and Structure* 5, National Biomedical Research Foundation, Washington, D.C. (1978), and in Argos, P. (1989) *EMBO J.* 8:779-785. For example, amino acids belonging to one of the following groups represent conservative changes or substitutions:

Ala, Pro, Gly, Gln, Asn, Ser, Thr:
Cys, Ser, Tyr, Thr;
Val, Ile, Leu, Met, Ala, Phe;
Lys, Arg, His;
Phe, Tyr, Trp, His; and
Asp, Glu.

"Homology," "homologs of," "homologous," "identity," or "similarity" refers to sequence similarity between two peptides, with identity being a more strict comparison. Homology and identity may each be determined by comparing a position in each sequence that may be aligned for purposes of comparison. When a position in the compared sequence is occupied by the same amino acid, then the molecules are identical at that position. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares 10% or less identity, with one of the sequences described herein. Related sequences share more than 10% sequence identity, such as at least about 15% sequence identity, at least about 20% sequence identity, at least about 30% sequence identity, at least about 40% sequence identity, at least about 50% sequence identity, at least about 60% sequence identity, at least about 70% sequence identity, at least about 80% sequence identity, at least about 90% sequence identity, at least about 95% sequence identity, or at least about 99% sequence identity.

The term "percent identity" refers to amino acid sequence identity between two peptides. Identity may be determined by comparing a position in each sequence that is aligned for purposes of comparison. When an equivalent position in one compared sequence is occupied by the same amino acid in the other at the same position, then the molecules are identical at that position; when the equivalent site occupied by the same or a similar amino acid residue (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ, FASTA and BLAST are available as part of the GCG sequence analysis package (University of Wisconsin, Madison, Wis.), and may be used with, e.g., default settings. ENTREZ is available through the National Center for Biotechnology Information, National Library of Medicine, NIH, Bethesda, Md.). In one embodiment, the percent identity of two sequences may be determined by the GCG program with a gap weight of 1, e.g., each amino acid gap is weighted as if it were a single amino acid mismatch between the two sequences. Other techniques for determining sequence identity are well known and described in the art.

2. Methods for Detecting Aβ Oligomer

Described herein are novel methods for detecting Aβ oligomer associated with Alzheimer's Disease in biological samples from a subject. The methodologies use flow cytometry and/or detect Aβ oligomer associated with cells present in or obtained from biological samples. The methods use peptide probes that preferentially bind to oliogomeric forms of Aβ protein, such as soluble Aβ oligomers, as described in greater detail further below.

U.S. Pat. No. 7,166,471 and U.S. Patent Application publications US 2006/0286672, US 2005/0026165, US 2008/0171341, US 2006/0057671, US 2008/0095706, and US 2010/0233095 describe peptide probes useful for the detection of, for example, misfolded proteins, target protein having a predominantly β-sheet secondary structure, and target protein in a specific state of self-aggregation. The peptide probes described in these references can be used in the methods described herein. Thus, the entire contents each of these patent documents are incorporated herein by reference in their entirety.

In specific embodiments, the peptide probe consists of from 10 to 34 amino acid residues comprising an amino acid sequence that is at least 70% identical to any one of SEQ ID NOs:1-56 and 62-65, preferentially binds to Aβ oligomers, and is labeled with a detectable label. In further specific embodiments, the peptide probe consists of SEQ ID NO:64.

(i) Flow Cytometry

Flow cytometry is a fluid-based detection technique that passes cells or particles in a liquid biological sample through a detector, and permits the detection of the cells or particles. Once detected, the cells or particles can be sorted depending on size or any marker (e.g., fluorescent label) associated with the cell.

Prior to the present invention, it was not believed that flow cytometry could be used to detect complexes of peptide probes and Aβ oligomer because the complexes were thought to be too small to be detected. Where flow cytometry has been used to detect Aβ protein complexes, the complexes contained an antibody and/or a solid bead platform, which are much larger complexes. See, e.g., Santos et al., Journal of Alzheimer's Disease, 11:117-125 (2007); EP 1882944; Santos et al., Journal of Alzheimer's Disease, 14:127-131 (2008). However, it was surprisingly discovered that flow cytometry can be used in the methods described herein.

Exemplary methods comprise preparing a test sample comprising the biological sample and a peptide probe as described herein, wherein the peptide probe is labeled with a detectable label and forms complexes with any Aβ oligomer present in the biological sample, and subjecting the test sample to flow cytometry to detect the signal of any such complexes. In accordance with such methods, the signal of the complexes is directly correlated with the presence and amount of Aβ oligomers in the biological sample.

As noted above, the biological sample may comprise a sample of body fluid, such as whole blood, cerebrospinal fluid (CSF), and/or tissue homogenate (e.g., brain homogenate). In some embodiments, the sample comprises blood plasma, including platelet rich or platelet poor blood plasma.

In some embodiments, the sample comprises erythrocytes and/or may be a sample comprising isolated erythrocytes. In some embodiments, the sample comprises platelets and/or may be a sample comprising isolated platelets. In some embodiments, the sample comprises erythrocytes and platelets. In some embodiments, the sample does not include cells.

In some embodiments, the label of the peptide probe is a fluorescent label, such as an FITC label.

In some embodiments, the Aβ oligomer is associated with a cell present in the biological sample, such as with an erythrocyte or platelet present in the biological sample, as discussed in more detail below. In some embodiments, the complex comprises peptide probe, Aβ oligomer, and a cell from the biological sample.

(ii) Cell-Associated Aβ Oligomer

While not wanting to be bound by any theory, it is believed that certain cells may be involved in the transport of Aβ protein in vivo, such as erythrocytes, platelets, and/or leukocytes, and that endogenous Aβ oligomers may be associated with such cells. Further, endogenous Aβ oligomers may be associated with tissue cells, such as neurological tissue cells, such as brain tissue cells. For example, Aβ oligomer may be associated with such cells such as by being bound (covalently or otherwise) on the cell surface, in the cell membrane, or intracellularly.

The present invention provides in vitro methods of detecting Aβ oligomer associated with cells, such as erythrocytes, platelets, leukocytes and/or tissue cells. In some embodiments, the methods comprise contacting cells ex vivo with a peptide probe that preferentially binds to Aβ oligomers and is labeled with a detectable label, such that the peptide probe forms a complex with Aβ oligomer associated with cells; and detecting a signal of the complex.

The label of the peptide probe can be any detectable label, and the signal can be detected by any suitable detection method, including flow cytometry, direct detection such as using fluorescence microscopy, fluorescence-activated cell sorting and fluorescence spectroscopy. In some embodiment, the label is a fluorescent label, while in other embodiments, the label is another detectable label, such as an excimer-forming pyrene moiety, or any other suitable detectable label, such as the labels discussed in more detail below.

In specific embodiments, a sample, such as a biological sample from a subject, comprises multiple cell types (e.g., erythrocytes and platelets) and is subjected to flow cytometry that separates complexes formed with each cell type, as noted above. For example, in some embodiments, the flow cytometry separately detects the signal of complex associated with erythrocytes and the signal of complex associated with platelets, such as based on the different sizes of such complexes.

(iii) Aβ Oligomer Load

In some embodiments, the methods comprise determining an Aβ oligomer load of the subject. As noted above, while not wanting to be bound by any theory, it is believed that certain cells may be involved in the transport of Aβ protein in vivo, such as erythrocytes, platelets, and/or leukocytes, and that such cells may be loaded with endogenous Aβ oligomers. Further, endogenous Aβ oligomers may be associated with tissue cells, such as neurological tissue cells, such as brain tissue cells. It is believed that by determining the degree of Aβ oligomer loading of such cells, one can assess the risk, presence, progression, severity and/or prognosis of Alzheimer's disease in the subject, with higher loading generally being indicative of greater disease progression.

In some embodiments, Aβ oligomer load is determined by detecting Aβ oligomer associated with cells present in a biological sample obtained from a subject, such as by preparing a first test sample comprising a biological sample from the subject that comprises cells and a peptide probe as described herein that is labeled with a detectable label and forms a first complex with Aβ oligomer associated with cells in the biological sample; detecting a signal of the first complex in the first test sample; preparing a second test sample comprising a biological sample from the subject that comprises cells, synthetic Aβ oligomer, and the peptide probe, wherein the peptide probe forms second complexes with Aβ oligomer associated with cells in the biological sample and with synthetic Aβ oligomer; and detecting a signal of the second complexes in the second test sample.

In accordance with such methods, a difference between the signal of the first complex in the first test sample and the signal of the second complexes in the second test sample is inversely correlated with the Aβ oligomer load of the subject. That is, if the second test sample exhibits a significantly greater signal than the first, that indicates that the cells were not fully loaded with endogenous Aβ oligomer, but were susceptible to further loading with synthetic Aβ oligomer, which resulted in the greater signal. On the other hand if the second test sample does not exhibit a greater signal than the first, that indicates that the cells were loaded with endogenous Aβ oligomer, and so were not very susceptible to further loading with synthetic Aβ oligomer.

In accordance with these methods, any sample can be used that includes cells that may be loaded with endogenous Aβ oligomer, such as erythrocytes, platelets, leukocytes, or tissue cells, such as cells from neurological tissue or brain.

In some embodiments, the second test sample is prepared by combining the biological sample and synthetic Aβ oligomer and then adding the labeled peptide probe. Such embodiments permit the synthetic Aβ oligomer to associate with cells in the biological sample before the peptide probe is added.

The label of the peptide probe can be any detectable label, and the signals can be detected by any suitable detection method, including flow cytometry, direct detection such as using fluorescence microscopy, fluorescence-activated cell sorting and fluorescence spectroscopy. In some embodiment, the label is a fluorescent label, while in other embodiments, the label is another detectable label, such as an excimer-forming pyrene moiety, or any other suitable detectable label, such as the labels discussed in more detail below.

In some embodiments, different signals corresponding to Aβ oligomer associated with different cell types are detected, such as by flow cytometry as discussed above.

(iv) Additional Detection Methods

As noted above, in some embodiments detection methods other than flow cytometry are used in the methods described herein. In some embodiments, assays similar to immunoassays but using a peptide probe as described herein instead of an antibody are used to detect Aβ oligomer in a biological sample. Such methods are referred to as a peptide-linked immunosorbent assay (i.e., "PLISA"). In specific embodiments, the PLISA can be a sandwich assay or a competitive assay. In some embodiments, the PLISA uses a solid-phase such as a plate that can be used in a fluorescence detection apparatus, such as a fluorescence plate reader, or a bead with capture antibody or capture peptide attached thereto. Such methods are described in WO 2012/149145; WO 2011/149917; US 2012/0282169; US 2010/0233095; US 2008/

0095706; U.S. Pat. No. 8,372,593; and WO 2006/031644, the content of which are incorporated herein by reference in their entirety.

In some embodiments, a combination of detection methods is used to detect Aβ oligomer. In specific embodiments, a combination of flow cytometry and non-flow cytometry methods are used to detect Aβ oligomer.

3. Synthetic Aβ Oligomers

As noted above, some of the methods described herein use synthetic Aβ oligomers. Synthetic Aβ oligomers include stabilized synthetic Aβ oligomers as described in WO 2011/149917, the contents of which are incorporated herein by reference in their entirety. The synthetic Aβ oligomers can include covalent and/or noncovalent complexes of Aβ monomers, and may comprise several to several hundred monomer units. In some embodiments, the synthetic Aβ oligomers are about 5 to 50 amino acids, about 10 to 40, about 15-30, or about 20, including about 5 to about 40, about 5 to about 30, about 5 to about 20, about 5 to about 15, about 5 to about 10, about 10 to about 50, about 10 to about 40, about 10 to about 30, about 10 to about 20, about 20 to about 50, about 20 to about 40, about 20 to about 30, about 30 to about 50, about 30 to about 40, or about 40 to about 50 amino acids. The monomers can comprise one or more of Aβ3-42, Aβ37, Aβ38, Aβ39, Aβ40 and Aβ42.

4. Peptide Probes

As noted above, peptide probes described herein preferentially bind to Aβ oligomer, and thus are useful for detecting Aβ oligomer. In some embodiments, the peptide probe preferentially binds soluble Aβ oligomer, as compared to Aβ monomer and higher order Aβ protein aggregates such as insoluble oligomers, insoluble amorphous self-aggregates, protofibrils or fibrils.

As noted above, U.S. Pat. No. 7,166,471 and U.S. Patent Application publications US 2006/0286672, US 2005/0026165, US 2008/0171341, US 2006/0057671, US 2008/0095706, and US 2010/0233095 describe peptide probes that can be used in the methods described herein. In specific embodiments, the peptide probe consists of from 10 to 34 amino acid residues comprising an amino acid sequence that is at least 70% identical to any one of SEQ ID NOs:1-56 and 62-65, preferentially binds to Aβ oligomers, and is labeled with a detectable label. In further specific embodiments, the peptide probe consists of SEQ ID NO:64.

In some embodiments the peptide probe does not include the full-length sequence of the Aβ protein, such as Aβ40 or Aβ42. In some embodiments, the peptide probe consists of from about 10 to about 34 amino acids, about 10 to about 30 amino acids, about 10 to about 25 amino acids, about 10 to about 20 amino acids, about 10 to about 15 amino acids, about 15 to about 34 amino acids, about 15 to about 30 amino acids, about 15 to about 25 amino acids, about 15 to about 20 amino acids, about 20 to about 34 amino acids, about 20 to about 30 amino acids, about 20 to about 25 amino acids, or any other range between about 10 to about 34 amino acids. In further embodiments, the probes about 10 amino acids, about 15 amino acids, about 20 amino acids, about 25 amino acids, about 30 amino acids, about 34 amino acids, or any other number between about 10 and about 34 amino acids. Probes of different lengths may exhibit different degrees of interaction and binding to Aβ oligomer, and suitable lengths can be selected by the skilled artisan guided by the teachings herein.

The probe may comprise a minimum number of contiguous amino acids of the Aβ protein, such as at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 34 contiguous amino acids of the Aβ protein, or any range between these numbers, such as about 10 to about 25 contiguous amino acids of the Aβ protein sequence.

The probe may comprise a maximum number of contiguous amino acids of the Aβ protein, such as up to about 5, up to about 6, up to about 7, up to about 8, up to about 9, up to about 10, up to about 11, up to about 12, up to about 13, up to about 14, up to about 15, up to about 16, up to about 17, up to about 18, up to about 19, up to about 20, up to about 21, up to about 22, up to about 23, up to about 24, up to about 25, up to about 30, or up to about 34 contiguous amino acids of the Aβ protein sequence, or any range between these numbers, such as about 10 to about 25 contiguous amino acids of the Aβ protein sequence.

In some embodiments, the probes may or may not undergo a conformation shift upon association with Aβ oligomer. In some embodiments, association of the peptide probe with Aβ oligomer is detected independently of any conformational shift that may or may not occur, such as by direct detection of probe associated with target oligomer, such as by detection of a detectable label on probe associated with target oligomer. In some embodiments, the association is temporary, such as an initial association of the probe with the Aβ oligomer and a later dissociation of the probe from the Aβ oligomer. Detectable labels are described in greater detail below.

In some embodiments, the peptide probe comprises an amino acid sequence of the Aβ protein that undergoes a conformational shift, such as a shift from an α-helix/random coil conformation to a β-sheet conformation, or comprises a variant of such a sequence. For example, amino acids 16-35 of the Aβ protein are known to comprise a β-sheet forming region. Thus, the probe may comprise amino acids 16-35 or 17-35 of the Aβ protein, or an amino acid sequence that is a variant thereof. The probe may also comprise amino acids 3-35 or 5-42 of the Aβ protein, or an amino acid sequence that is a variant thereof. The amino acid sequence of the peptide probe may be designed, therefore, from the Aβ protein sequence, based on existing sequence and conformation information or, alternatively, may be readily determined experimentally.

In some embodiments, the peptide probes are capable of adopting both a primarily random coil/alpha-helix conformation and a primarily β-sheet conformation, and adopt a primarily β-sheet conformation upon binding to target oligomer exhibiting a primarily β-sheet conformation. In some embodiments the peptide probe is provided in a primarily α-helix/random coil conformation, and undergoes a conformation shift to a primarily β-sheet conformation upon contact, binding, association and/or interaction with Aβ oligomer in a primarily β-sheet conformation. In other embodiments, the peptide probe shifts conformation by becoming more condensed, more diffuse, or adopting any different configuration. In some embodiments, the peptide probe more closely adopts the conformation of the Aβ oligomer. The probe may be provided in any physiologically acceptable solution. For example, the probe may be prepared as a trifluoracetic salt and resuspended in an organic solvent, such as 100% hexafluorisopropanol (HFIP) or 50% acetonitrile (ACN).

In some embodiments, the peptide probe comprises a variant sequence based on a corresponding region of the Aβ protein sequence. The variant sequence may comprise one or more amino acid additions, substitutions or deletions relative to the Aβ protein sequence, such that the variant sequence (or the peptide probe as a whole) has an amino acid sequence having at least 60%, at least 75%, at least 80%, at least 85%, at least 90%, at least 95%, or 100% identity to the Aβ protein sequence. In some embodiments, the peptide probe may have an amino acid sequence with one or more additional amino acids at either terminus, or at both termini, as compared to the reference sequence. Additions, substitutions, and deletions may also be made at an internal portion of the reference sequence, or both internally and terminally. In some embodiments, the peptide probe further comprises the addition of a lysine residue at the C-terminus, or another label to facilitate purification and/or labeling.

The reference sequence may comprise a minimum number of contiguous amino acids of the Aβ protein, such as at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35 contiguous amino acids of the Aβ protein sequence, or any range between these numbers, such as about 10 to about 25 contiguous amino acids of the Aβ protein sequence.

The reference sequence may comprise a maximum number of contiguous amino acids of the Aβ protein, such as up to about 5, up to about 6, up to about 7, up to about 8, up to about 9, up to about 10, up to about 11, up to about 12, up to about 13, up to about 14, up to about 15, up to about 16, up to about 17, up to about 18, up to about 19, up to about 20, up to about 21, up to about 22, up to about 23, up to about 24, up to about 25, up to about 30, or up to about 34 contiguous amino acids of the Aβ protein sequence, or any range between these numbers, such as about 10 to about 25 contiguous amino acids of the Aβ protein sequence.

As disclosed above, the variant sequence optionally may adopt either a more- or less-ordered conformation upon binding to a target protein exhibiting a β-sheet conformation. In some embodiments, for example, the target protein is Aβ protein, and the variant sequence comprises one or more substitutions selected from the group consisting of G29H, G29R, G29K, and G33E. Additionally or alternatively, the β-sheet structure of the variant sequence may be less thermodynamically strong than that of the reference sequence. In specific embodiments, the variant sequence comprises one or more substitutions selected from the group consisting of I32S, F19S, S26D, H29D, I31D, L34D, and L34P.

Additionally or alternatively, the variant sequence may have an increased hydrophilicity and/or solubility in aqueous solutions than the reference sequence. In specific embodiments, the variant sequence comprises one or more amino acid additions or substitutions that introduce a glutamic acid residue and/or a d-arginine residue. Additionally or alternatively, the variant sequence may be conjugated to a hydrophilic moiety, such as a soluble polyethylene glycol moiety.

In some embodiments, the variant sequence comprises the substitution of at least one residue with a glutamic acid residue. In some embodiments, the variant sequence comprises the substitution of at least one residue with a histidine residue. In some embodiments, the variant sequence comprises one or more substitutions selected from the group consisting of an isoleucine residue with a serine residue; glutamic acid residue with either a proline residue, a glycine residue, a glutamine residue or a lysine residue; a phenylalanine residue with a serine residue; a leucine residue with a proline residue; an alanine residue with a glycine residue; and an aspartic acid residue with an asparagine residue.

In some embodiments, the peptide probes described herein bind to Aβ protein oligomer and undergo a conformation shift upon such binding. The conformation shift may comprise a change in the distance between the N- and C-termini of the probe (or between any other two points), folding more or less compactly, changing from predominantly one secondary structure to predominantly another secondary structure, or any change in the relative amounts of different secondary structures, or any change in the relationship between any labels on the probes. In some embodiments, the probes are conformationally dynamic peptides based on the human Aβ sequence, as described in US 2010/0233095.

Any of the probes described herein can be presented in D- or L-enantiomeric form. Additionally or alternatively, the probes can be presented with an amino acid sequence in reverse order of the amino acid sequences described herein. For example, where a peptide probe is described as having an amino acid sequence A-B-C-D, the reverse sequence would be D-C-B-A. In some embodiments, the probes are presented in D- or L-enantiomeric form, and/or in reverse order.

Any of the probes described herein may be end-capped at one or both of the C-terminus and the N-terminus with a small hydrophobic peptide ranging in size from about 1 to about 5 amino acids. In some embodiments, one or both of the C-terminus and N-terminus has a lysine residue, such as to facilitate labeling. Additionally or alternatively, one or both of the C-terminus and N-terminus has a cysteine residue. Additionally or alternatively, any of the probes described herein may be modified by the substitution of a methionine residue with a residue resistant to oxidation, such as an alanine residue. Additionally or alternatively, any of the probes described herein may be modified by the substitution of at least three consecutive residues of the reference sequence with alanine residues.

In some embodiments, the peptide probe is labeled with two pyrene labels, one on the N-terminal amine and the other on a side chain of a C-terminal lysine residue. In specific embodiments, the pyrene label is PBA. In some embodiments, the peptide probe contains a C-terminal amide in place of the carboxyl group.

In accordance with any of the foregoing embodiments, the peptide probe may be conjugated to a biotin moiety, such as through a peptide linker. In specific embodiments, the peptide linker is selected from the group consisting of a flexible linker, a helical linker, a thrombin site linker and a kinked linker. In other embodiments, the peptide probe is conjugated to a biotin moiety through a side chain of an internal lysine residue. Other appropriate peptide linkers are described in the art (see, e.g., U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

For example, biotinylation can be achieved through a helical linker such as EAAAK (SEQ ID NO:57) at the C-terminus, as illustrated by AD310 (SEQ ID NO:38). In general, a helical linker includes residues that form alpha helixes, such as alanine residues. Alternatively, biotinylation can be achieved through a side chain on a lysine residue, including an internal or terminal lysine residue, as illustrated by AD313 (SEQ ID NO:39). Alternatively, biotinylation can be achieved through a flexible linker (such as GSSGSSK (SEQ ID NO:58)) at the C-terminus, as illustrated by AD314 (SEQ ID NO:40). In general, a flexible linker includes one or more glycine and/or serine residues, or other residues that can freely rotate about their phi and psi angles. Alternatively, biotinylation can be achieved through a thrombin site linker (such as a linker comprising LVPRGS (SEQ ID NO:59), such as GLVPRGSGK (SEQ ID NO:60)) at the at the C-terminus, as illustrated by AD317 (SEQ ID NO:41). Alternatively, biotinylation can be achieved through a kinked linker (such as PSGSPK (SEQ ID NO:61)) at the at the C-terminus, as illustrated by AD321 (SEQ ID NO:42). In general, kinked linkers comprise one or more proline residues, or other residues that have fixed phi and psi angles that rigidly project the biotin moiety away from the peptide probe's protein-binding motif.

In some embodiments, the probes are selected from SEQ ID NOs:1-56, or from SEQ ID NOs:1-56 and 62-65. In some specific embodiments, the probes are selected from the group consisting of SEQ ID NOs:2, 22, 23, 41, 56, 62, 63, 64, or 65. In some embodiments, the probes are PEP-10, PEP-11 and PEP-12. Probes described in US 2008/0095706 for targeting Aβ protein, and probes designed in accordance with US 2010/0233095, may be used as described herein. The contents of these applications are incorporated herein by reference in their entirety.

In specific embodiments, the probe may consist of two point mutations (e.g., SEQ ID NO:2; SEQ ID NO:62); the addition of two d-Arginine residues (r) (e.g., SEQ ID NO:22; SEQ ID NO:56; SEQ ID NO:62; SEQ ID NO:64); combinations of mutations described herein (e.g., SEQ ID NO:23; SEQ ID NO:62); a naturally-occurring "Italian" mutant (SEQ ID NO:56); or addition of a linker and biotin (e.g., SEQ ID NO:41).

In some embodiments, the one or more amino acid additions, substitutions or deletions may introduce a salt bridge between two residues, such as between a glutamic acid residue and a histidine residue, a glutamic acid residue and an arginine residue, and/or a glutamic acid residue and a lysine residue. Further, the amino acid additions, substitutions, or deletions may introduce an Aβ binding motif into the peptide probe, such as a GXXEG motif (SEQ ID NO:25).

Exemplary peptide probes designed in accordance with the principles described above are set forth in Table 1. Highlighting shows amino acid substitutions relative to the wildtype sequence and/or labels. As shown by shading in the sequences in the table, most of the peptide sequences are based on amino acids 16-35 of the Aβ peptide, which is a β-sheet forming region of the Aβ peptide (others are based on longer portions of the Aβ peptide), with an added C-terminal lysine residue to facilitate labeling. Other peptide sequences are based on amino acids 17-35 of the Aβ peptide. The category (or categories) of the sequence variants are indicated in the table (e.g., modified to improve stability, provide a salt bridge, increase solubility, facilitate alpha-helix formation, destabilize β-sheet structure, add an Aβ binding motif, etc.). Also illustrated are options for peptide probe labeling, including different label sites and label pairs.

The following abbreviations are used in Table 1:
"PBA"=pyrene butyric acid
"r"=d-Arginine
"Dabcyl"=4-(4-dimethylaminophenyl) diazenylbenzoic acid
"EDANS"=5-(2'-aminoethyl)aminonaphthalene-1-sulfonic acid
"FAM"=5(6)carboxyfluorescein
"Dansyl"=5-dimethylaminonaphthalene-1-sulfonyl
"FITC"=Fluorescein isothiocyanate
"Ahx"=aminohexyl The above features are optional for the peptide probes described herein. Although the probes in Table 1 are depicted as having or not having these features, any of the probes listed in the table and any of the probes described herein can have or lack one or more of these features.

The probe may alternatively be a peptide mimic ("peptoid") of any of the peptide probes described herein. In some embodiments, the probe is a peptide mimic that has a natural peptide backbone but has non-natural amino acids or chemical moieties. In other embodiments, the probe is a peptide mimic that has a non-peptide backbone and comprises a chemical backbone, such as a polymeric backbone. In some embodiments, a peptide mimic exhibits increased stability over the corresponding peptide.

Additional probes may be designed and tested for use in the present methods. Briefly, peptides and peptide mimics may be computationally designed to closely match hydrophobic topology and intramolecular pair contacts to wild type Aβ peptide and/or a probe with the desired characteristics as described above. Algorithms for designing such peptides and peptide mimics are known in the art. See, e.g., Mobley, D. L., et al., Structure 2009, 17, (4), 489-98; Fennell, C. J., et al., J Phys Chem B 2009; Voelz, V. A., et al., PLoS Comput Biol 2009, 5, (2), e1000281.; Shell, M. S., et al., Biophys J 2009, 96, (3), 917-24; Mobley, D. L., et al., J Chem Theory Comput 2007, 3, (4), 1231-1235; Wu, G. A., et al., Structure 2008, 16, (8), 1257-66; Chorny, I., et al., J Phys Chem B 2005, 109, (50), 24056-60.

5. Labels

As noted above, the peptide probes disclosed herein may comprise one or more detectable labels. For example, the peptide probe may be coupled or fused, either covalently or non-covalently, to a label, with or without a linker. Also as noted above, in some embodiments, the label is detectable independent of the conformation of the probe and/or independent of any conformation shift or association with the Aβ oligomer.

In some embodiments, a label is selected to permit direct detection of probe associated with Aβ oligomer. Thus, for example, one or more labels may be detectable by direct detection, such as fluorescent labels, radioactive labels, etc. In some embodiments, the label is a fluorescent label, such as FITC. In other embodiments, the label is pyrene, such as a pyrene excimer. Such association may be current probe association with Aβ oligomer or past probe association with Aβ oligomer. Additional labels are described below.

In some embodiments, a peptide probe may be labeled with a detectable label at the N-terminus, the C-terminus, both termini, or at one or more positions (including a side chain) that is detectable independent of the conformation or conformational transition of the probe.

In some embodiments, a peptide probe may be labeled with a detectable label at the N-terminus, the C-terminus, both termini, or at one or more positions that generate a signal when the peptide associates with target protein or adopts a β-sheet conformation or undergoes a conformation change upon binding to target protein. Thus, for example, the label sites may be selected from (i) the N-terminus and the C-terminus; (ii) the N-terminus and a separate site other than the C-terminus; (iii) the C-terminus and a separate site other than the N-terminus; and (iv) two sites other than the N-terminus and the C-terminus The peptide probe may be labeled with two or more labels, wherein the distance between two or more labels on the peptide probe when the peptide probe is bound to target protein is different than the distance when the peptide probe is not bound to target protein. The peptide probe may additionally or alternatively be labeled with a detectable label pair selected from an excimer pair, a FRET pair and a fluorophore/quencher pair. When the peptide probe is labeled with an excimer pair, such as a pyrene pair, it may emit an excimer signal when the peptide probe exhibits a β-sheet conformation. When the peptide probe is labeled with a FRET pair, such as DACIA-I/NBD, Marina Blue/NBD, Dansyl/Trp, and EDANS/FAM, it may emit a fluorescence resonance transfer (FRET) signal when the peptide probe exhibits a β-sheet conformation. When the peptide probe is labeled with a fluorophore/quencher pair, such as pyrene/Dabcyl, EDANS/Dabcyl and FAM/Dabcyl, the fluorophore signal may be quenched when the peptide probe exhibits a β-sheet conformation.

In some embodiments, the labels and label sites are selected such that the labels do or do not interact based on the conformation of the probe, for example, such that the labels do not interact when the probe is in its unassociated conformation and do interact when the probe undergoes a conformation shift upon association with target protein, to generate a detectable signal (including quenching), or vice versa. This may be accomplished by selecting label sites that are further apart or closer together depending on the associated state of the probe, e.g., depending on whether the probe has undergone a conformation shift upon association with target protein. In some embodiments, the magnitude of the signal associated with the associated probe is directly correlated to the amount of target protein detected. Thus, the methods of the present invention permit detection and quantification of target protein.

For example, excimer, FRET or fluorophore/quencher label pairs may be used to permit detection of a specific conformation of the probe, such as the conformation adopted when the probe associates with Aβ protein aggregates associated with amyloidogenic disease. In these embodiments, the probe is labeled at separate sites with a first label and a second label, each being complementary members of an excimer, FRET or fluorophore/quencher pair.

For example, excimer-forming labels may emit their monomeric signals when the probe is in its unassociated state, and may emit their excimer signal when the probe undergoes a conformation shift that brings the labels in closer physical proximity, upon association with the target protein. Similarly, FRET labels may emit their FRET signal when the probe undergoes a conformation shift that brings the labels in closer physical proximity. On the other hand, fluorophore/quencher label pairs may emit the fluorophore signal when the probe is in its unassociated state, and that signal may be quenched when the probe undergoes a conformation shift that brings the labels in closer physical proximity. As noted above, the labels may be sited such that the opposite change in signal occurs when the probe undergoes a conformation shift upon association with the target protein.

In accordance with any of the foregoing, a detectable label may be conjugated to a side chain of a terminal lysine residue of the peptide probe, and/or to a side chain of an internal lysine residue of the peptide probe.

In some embodiments, the detectable label is attached to the probe by a linker. In specific embodiments, the peptide linker is selected from the group consisting of a flexible linker, a helical linker, a thrombin site linker and a kinked linker. In specific embodiments, the linker is an aminohexyl linker. In other embodiments, the peptide probe is conjugated to a linking through a side chain of an internal lysine residue. Other appropriate peptide linkers are described in the art (see, e.g., U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

Any of the probes described herein may include a dipyrene butyrate (PBA) moiety at the N-terminus and/or one extending from a lysine side chain near the C-terminus, and/or at any other site suitable for labeling. Additionally or alternatively, any of the probes described herein may have been modified to include an amide group at the C-terminus, in place of the naturally occurring carboxyl group.

Moreover, while some of these embodiments have been described with reference to the use of two labels per peptide probe, it should be understood that multiple labels could be used. For example, one or more labels could be present at each labeling site, or multiple labels could be present, each at different labeling sites on the probe. In these embodiments, the labels may generate independent signals.

Exemplary labels for use in any of these embodiments include fluorescent agents (e.g., fluorophores, fluorescent proteins, fluorescent semiconductor nanocrystals), phosphorescent agents, chemiluminescent agents, chromogenic agents, quenching agents, dyes, radionuclides, metal ions, metal sols, ligands (e.g., biotin, streptavidin haptens, and the like), enzymes (e.g., beta-galactosidase, horseradish peroxidase, glucose oxidase, alkaline phosphatase, and the like), enzyme substrates, enzyme cofactors (e.g., NADPH), enzyme inhibitors, scintillation agents, inhibitors, magnetic particles, oligonucleotides, and other moieties known in the art.

In specific embodiments, the fluorophore label is indocyanine green (ICG), Cypate, Cy3, Cy5, Cy7 or FITC. These and other directly detectable labels are useful in embodiments where the peptide probe may not undergo a conformational shift or transformation when associated with Aβ oligomer. In some embodiments, the directly detectable labels are detected using fluorescence microscopy, fluorescence-activated cell sorting of fluorescence spectroscopy.

As noted above, in some embodiments, the label comprises a pyrene moiety. As used herein, a pyrene moiety includes pyrene, which comprises four fused benzene rings or a derivative of pyrene. By pyrene derivative is meant a molecule comprising the four fused benzene rings of pyrene, wherein one or more of the pyrene carbon atoms is substituted or conjugated to a further moiety. Exemplary pyrene derivatives include alkylated pyrenes, wherein one or more of the pyrene carbon atoms is substituted with a linear or branched, substituted or unsubstituted, alkyl, alkenyl, alkynyl or acyl group, such as a $C_1$-$C_{20}$, linear or branched, substituted or unsubstituted alkyl, alkenyl, alkynyl or acyl group, where the group may be substituted with, for example, a moiety including an O, N or S atom (e.g., carbonyl, amine, sulfhydryl) or with a halogen. In some embodiments the pyrene derivative includes one or more free carboxyl groups and/or one or more free amine groups, each of which may be directly attached to a pyrene carbon atom or attached to any position on a linear or branched, substituted or unsubstituted, alkyl, alkenyl, alkynyl or acyl group as described above, such as being attached at a carbon atom that is separated from a pyrene carbon by 1 or more, such as 1 to 3, 1 to 5, or more, atoms. In some embodiments, the pyrene is substituted with one or more acetic acid moieties and/or one or more ethylamine moieties. In some embodiments, the pyrene derivative is substituted with a single methyl, ethyl, propyl or butyl group. In some embodiments, the pyrene is substituted with a short chain fatty acid, such as pyrene butyrate. In another embodiment, the pyrene is conjugated to albumin, transferring or an Fc fragment of an antibody. In some embodiments, the substituent is attached to pyrene through a carbon-carbon linkage, amino group, peptide bond, ether, thioether, disulfide, or an ester linkage. In other embodiments, the pyrene derivative is PEGylated pyrene, i.e., pyrene conjugated to polyethylene glycol (PEG). Such pyrene derivatives may exhibit a longer circulating half-life in vivo. In other embodiments, the pyrene derivative is pyrene conjugated to albumin.

In some embodiments, the label comprises a fluorescent protein which is incorporated into a peptide probe as part of a fusion protein. Fluorescent proteins may include green fluorescent proteins (e.g., GFP, eGFP, AcGFP, TurboGFP, Emerald, Azami Green, and ZsGreen), blue fluorescent proteins (e.g., EBFP, Sapphire, and T-Sapphire), cyan fluorescent proteins (e.g., ECFP, mCFP, Cerulean, CyPet, AmCyan1, and Midoriishi Cyan), yellow fluorescent proteins (e.g., EYFP, Topaz, Venus, mCitrine, YPet, PhiYFP, ZsYellow1, and mBanana), and orange and red fluorescent proteins (e.g., Kusabira Orange, mOrange, dTomato, dTomato-Tandem, DsRed, DsRed2, DsRed-Express (T1), DsREd-Monomer, mTangerine, mStrawberry, AsRed2, mRFP1, JRed, mCherry, HcRed1, mRaspberry, HcRed-Tandem, mPlum and AQ143). Other fluorescent proteins are described in the art (Tsien, R. Y., Annual. Rev. Biochem. 67:509-544 (1998); and Lippincott-Schwartz et al., Science 300:87-91 (2003)). These and other directly detectable labels are useful in embodiments where the peptide probe may not undergo a conformational shift or transformation when associated with Aβ oligomer.

The fluorescent protein as part of a fusion protein may be coupled via a peptide linker as described in the art (U.S. Pat. No. 6,448,087; Wurth et al., J. Mol. Biol. 319:1279-1290 (2002); and Kim et al., J. Biol. Chem. 280:35059-35076 (2005), which are incorporated herein by reference in their entireties). In some embodiments, suitable linkers may be about 8-12 amino acids in length. In further embodiments, greater than about 75% of the amino acid residues of the linker are selected from serine, glycine, and alanine residues.

As used herein, a "fluorophore" is a chemical group that may be excited by light to emit fluorescence or phosphorescence. A "quencher" is an agent that is capable of quenching a fluorescent signal from a fluorescent donor. A first fluorophore may emit a fluorescent signal that excites a second fluorophore. A first fluorophore may emit a signal that is quenched by a second fluorophore. The probes disclosed herein may undergo fluorescence resonance energy transfer (FRET).

Fluorophores and quenchers may include the following agents (or fluorophores and quenchers sold under the following tradenames): 1,5 IAEDANS; 1,8-ANS; umbelliferone (e.g., 4-Methylumbelliferone); acradimum esters, 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; Cypate; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrohodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrohodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; EDANS; Eosin; Erythrosin; Erythrosin ITC; Ethidium Bromide; Ethidium homodimer-1 (EthD-1); Euchrysin; Euko-Light; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro- Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF2); a fluorescent protein (e.g., GFP (S65T); GFP red shifted (rsGFP); GFP wild type, non-UV excitation (wtGFP); GFP wild type, UV excitation (wtGFP); and GFPuv); Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indocyanine Green (ICG); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; luminol, Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

6. Kits

Also provided are kits comprising the peptide probes, synthetic Aβ oligomers, and/or labels described herein. The kits may be prepared for practicing the methods described herein. Typically, the kits include at least one component or a packaged combination of components useful for practicing a method. By "packaged combination" it is meant that the kits provide a single package that contains a combination of one or more components, such as probes, buffers, instructions for use, and the like. A kit containing a single container is included within the definition of "packaged combination." The kits may include some or all of the components necessary to practice a method disclosed herein. Typically, the kits include at least one probe in at least one container. The kits may include multiple probes which may be the same or different, such as probes comprising different sequences and/or different labels, in one or more containers. Multiple probes may be present in a single container or in separate containers, each containing a single probe.

EXAMPLES

Example 1—Flow Cytometry Assay on Whole Blood

A. First Sample: Without Synthetic Aβ Oligomer

A first sample containing whole blood is obtained from a subject by venipuncture and collected in EDTA tubes. Peptide probe labeled with FITC (PEP-11) stored in organic solvent is brought to room temperature. The organic solvent is then removed by rotovaporation or air evaporation. The first sample is then diluted in HEPES-buffered saline and subsequently combined with the peptide probe solution. The resulting combination is stored in the dark at room temperature for up to an hour, in order to allow the labeled peptide probe to bind to (e.g., associate with and/or form a complex with) any Aβ oligomer associated with cells present in the first test sample.

B. Second Sample: With Synthetic Aβ Oligomer

A second sample containing whole blood is obtained in the same manner as described above. The second sample is then diluted in HEPES-buffered saline and subsequently combined with synthetic Aβ oligomer, allowing the synthetic Aβ oligomer to bind to cells (e.g., associate with and/or form a complex with) present in the second sample or any Aβ oligomer associated with the cells. Peptide probe labeled with FITC (PEP-11) stored in organic solvent is brought to room temperature and diluted with saline. The organic solvent is then removed by rotovaporation or air evaporation. The peptide probe is then combined with the second sample containing whole blood and synthetic Aβ oligomer. The combination is stored in the dark at room temperature, allowing the labeled peptide probe to bind to (e.g., associate with and/or form a complex with) any Aβ oligomer and synthetic Aβ oligomer associated with cells.

C. Flow Cytometry Analysis

After storage, the first and second samples are subjected to a FACScan flow cytometer in TruCount Tubes to isolate erythrocytes in the test samples. The erythrocytes in the test samples are gated in logarithmic forward/side scatter dot plots, and the fluorescence of the FITC labels are detected by appropriate bandpass filters.

Example 2—Flow Cytometry Assay on Erythrocytes in Whole Blood

First and second samples are obtained from a normal subject (i.e., does not have Alzheimer's Disease) and a subject with Alzheimer's Disease. The samples are processed and analyzed in accordance with the procedure in EXAMPLE 1.

FIG. 1 is a depiction of the first sample from each subject (i) before labeled peptide probe is added to the samples (left column); and (ii) after the labeled peptide probe is added to the samples (right column) As seen in the left column, endogenous Aβ oligomer is associated with erythrocytes to a greater degree in subjects with Alzheimer's disease. As seen in the right column, labeled peptide probe associates with (e.g., forms a complex with) Aβ oligomer associated with erythrocytes, permitting detection and quantification of endogenous Aβ oligomer associated with erythrocytes (e.g., by detection of peptide probe-Aβ oligomer-erythrocyte complexes).

Figure 2:
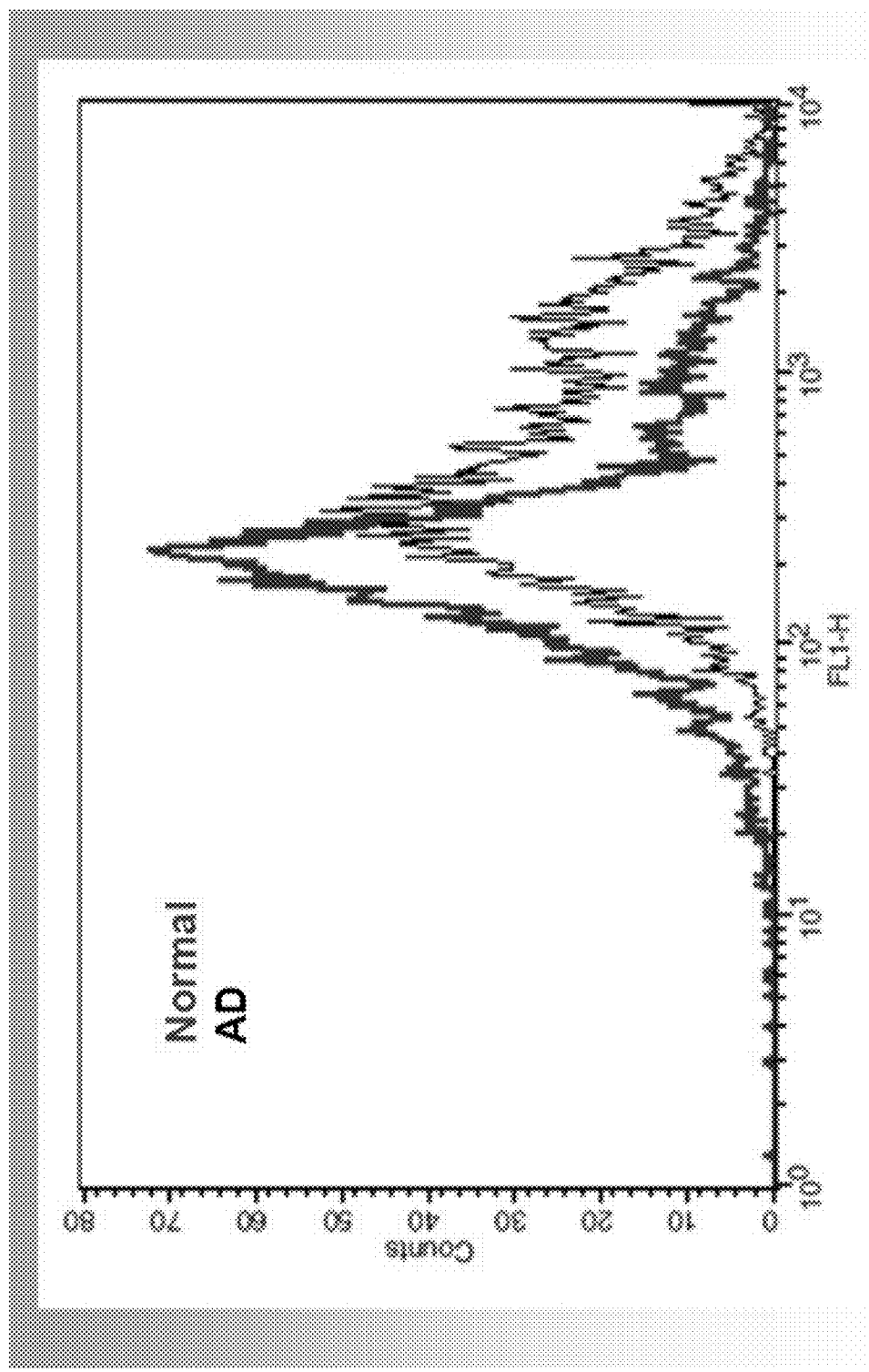
FIG. 2 depicts FITC signals from samples comprising whole blood samples containing erythrocytes from normal subjects or subjects with Alzheimer's Disease and PEP-11 peptide probe. The profiles reflect the amount of endogenous Aβ oligomer associated with erythrocytes in the sample.

FIG. 2 shows FITC signals from the first samples (endogenous Aβ oligomer only) probed with PEP-11 peptide probe (SEQ ID NO:64). Complexes comprising labeled peptide probe-endogenous Aβ oligomer-erythrocytes are detected. The signal (fluorescence intensity) corresponding to the subject with Alzheimer's Disease is great than that corresponding to the normal subject, reflecting the greater amount of Aβ oligomer present in the sample from the subject with Alzheimer's Disease.

Figure 3:
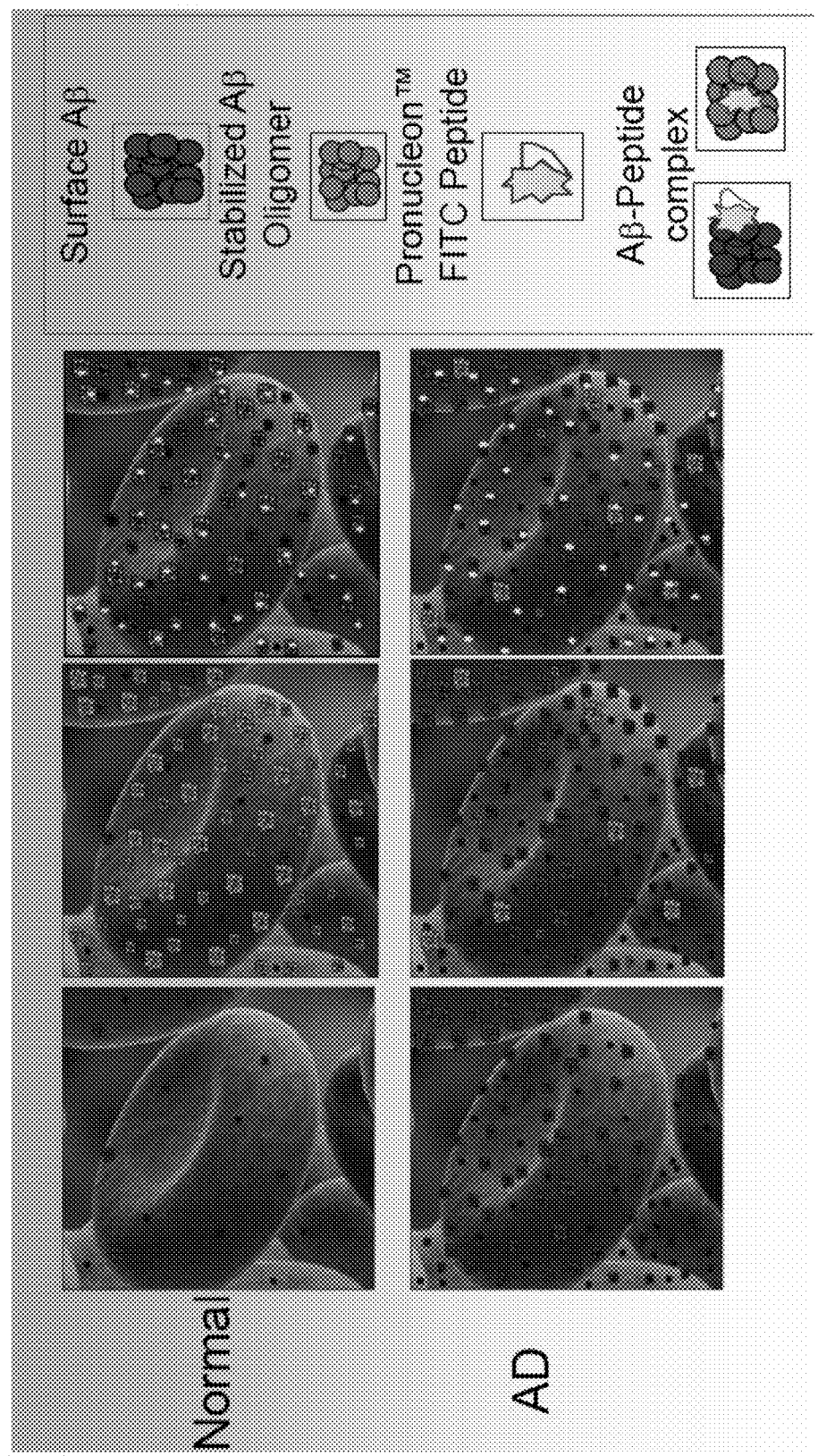
FIG. 3 depicts (i) endogenous Aβ oligomer associated with erythrocytes in whole blood samples from normal subjects or subjects with Alzheimer's Disease; (ii) samples with synthetic Aβ oligomer added; and (iii) complexes comprising labeled peptide probe and endogenous Aβ oligomer and complexes comprising labeled peptide probe and synthetic Aβ oligomer.

FIG. 3 is a depiction of the second sample from each subject (i) before synthetic Aβ oligomer or labeled peptide probe is added to the samples (left column); (ii) after the synthetic Aβ oligomer is added to the samples (middle column) and (iii) after the PEP-11 peptide probe is added to the samples (right column) As with FIG. 1, as seen in the left column, endogenous Aβ oligomer is associated with erythrocytes to a greater degree in subjects with Alzheimer's disease. As seen in the middle column, synthetic Aβ oligomers associate with erythrocytes to a greater degree in the sample obtained from the normal subject as compared to the sample from the subject with Alzheimer's Disease. Without being bound by theory, it is believed that erythrocytes in subjects with Alzheimer's Disease already are associated with endogenous Aβ oligomer and thus have less capacity for association with synthetic Aβ oligomer. As seen in the right column, labeled peptide probe associates with endogenous and synthetic Aβ oligomers.

Figure 4:
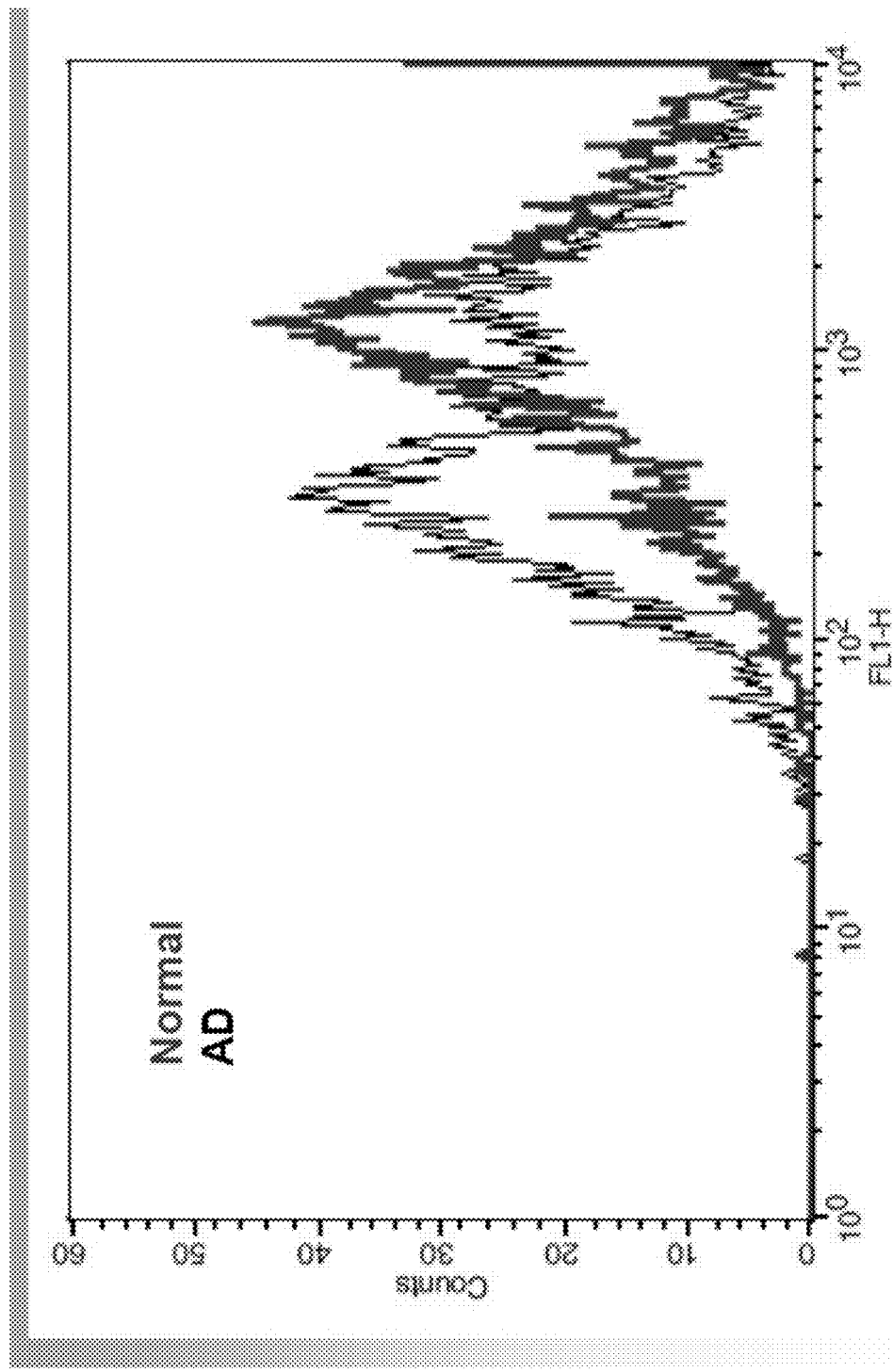
FIG. 4 depicts FITC signals from samples comprising (i) whole blood samples containing erythrocytes from normal subjects or subjects with Alzheimer's Disease and (ii) synthetic Aβ oligomer and (iii) PEP-11 peptide probe. The profiles reflect the total amount of endogenous and synthetic Aβ oligomer associated with erythrocytes in the sample.

FIG. 4 shows FITC signals from the second samples after the synthetic Aβ oligomer and labeled peptide probe are added to the samples. Complexes comprising labeled peptide probe-endogenous Aβ oligomer-erythrocytes and complexes comprising labeled peptide probe-synthetic Aβ oligomer-erythrocytes are detected. Comparing the figure to FIG. 2, the signal for the subject with Alzheimer's Disease is roughly the same as in FIG. 2, indicating that the amount of Aβ oligomer associated with erythrocytes is about the same before and after from the addition of synthetic Aβ oligomer. In contrast, the signal for the normal subject is significantly shifted to the right (e.g., a greater signal) in FIG. 2, indicating that the amount of Aβ oligomer associated with erythrocytes is greater after the addition of synthetic Aβ oligomer.

Figure 5:
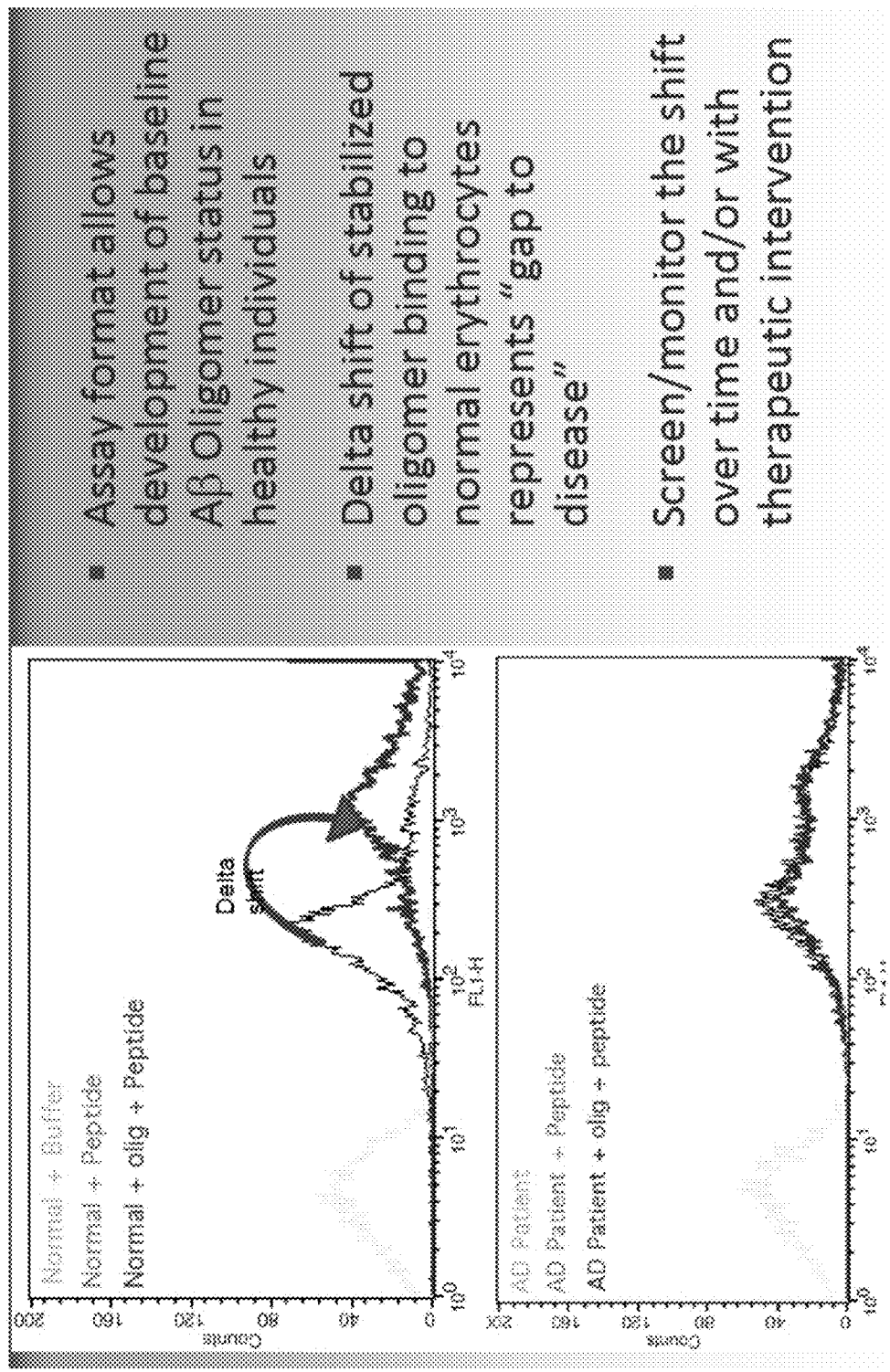
FIG. 5 overlays the FITC signals from FIGS. 2 and 4. For normal subjects, the overlay shows a significant difference in the signal, reflecting a significant difference in the endogenous versus final (endogenous plus synthetic) Aβ oligomer loading of the erythrocytes in the sample. For subjects with Alzheimer's Disease, the overlay shows little difference in the signal, reflecting a small difference in the endogenous versus final Aβ oligomer loading of the erythrocytes in the sample.

FIG. 5 overlays the signals from FIGS. 2 and 4 for the normal and AD subjects, and highlights the signal shift or "delta" (binding capacity) between the signal obtained with and without synthetic Aβ oligomer in the normal subject. It is believed that this signal shift is inversely correlated with the endogenous Aβ oligomer load of the erythrocytes, and thus the Aβ oligomer load of the subject, with a greater signal shift being correlated a low Aβ oligomer load and thus normal (non-AD) disease state, and a small signal shift being associated with a higher Aβ oligomer load and thus a higher risk of disease or more advanced disease state.

These data illustrate how the methods of EXAMPLE 1 and 2 can be used to distinguish between a normal subject and a subject with Alzheimer's Disease. Furthermore, this assay format could be used to provide a baseline Aβ oligomer load status of a normal subject that could be monitored over time for the risk or development of disease. Likewise, this assay format could be used to provide a baseline Aβ oligomer load status of an AD subject that could be monitored over time for the progression of disease and/or success of therapeutic treatments.

Figure 6:
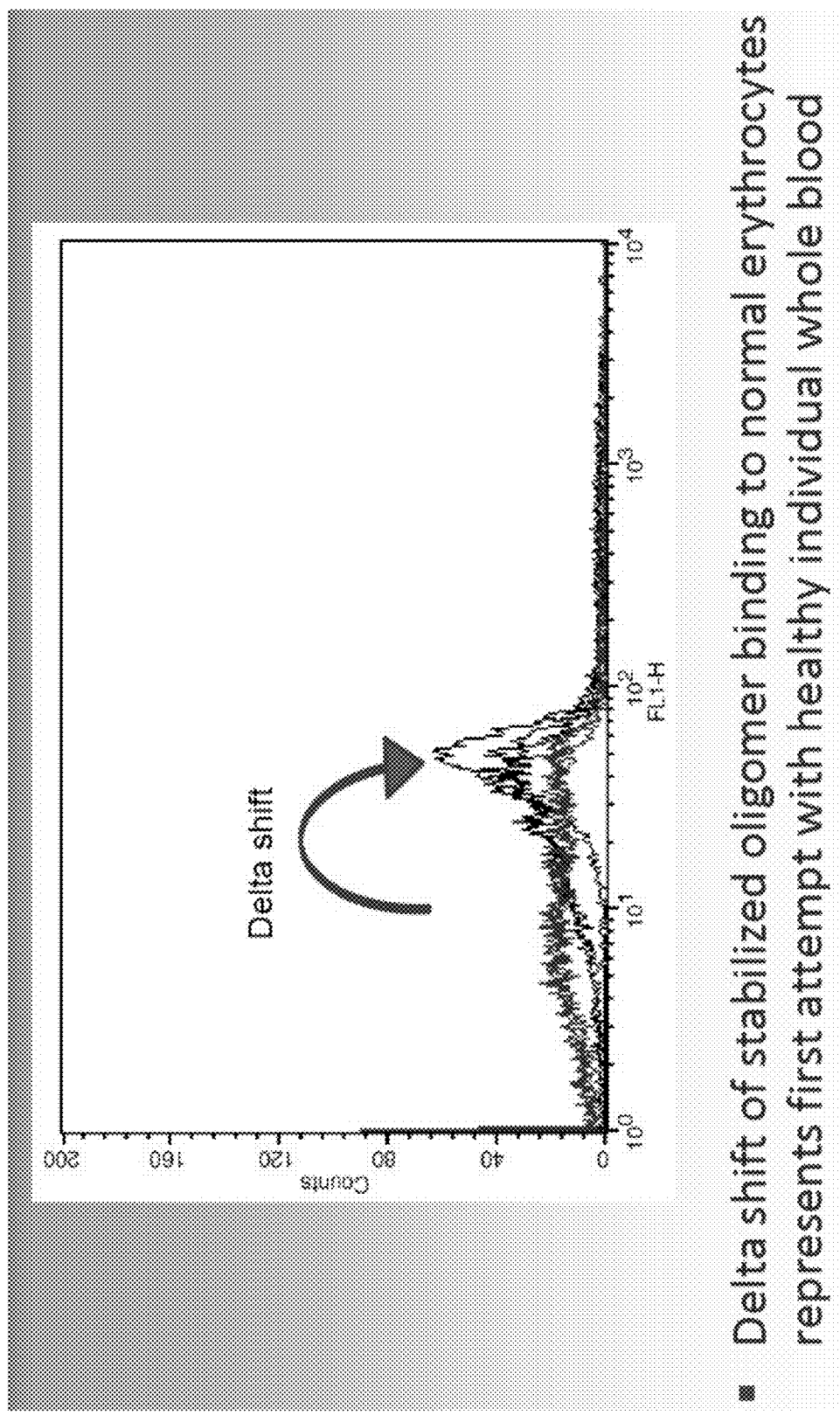
FIG. 6 depicts the overlay of FITC signals from a sample of whole blood from a normal human patient and PEP-11, without and with synthetic Aβ oligomer.

A sample of whole blood was obtained from another normal subject and processed as indicated in EXAMPLE 1. FIG. 6 depicts the delta shift (binding capacity) between the signal of the first (no synthetic Aβ oligomer) and second (synthetic Aβ oligomer) samples.

Example 3—Flow Cytometry on Platelets in Plasma

A first sample containing platelet rich plasma (PRP) is obtained by separating whole blood or from a frozen sample of previously separated whole blood. The first sample is verified to contain PRP by flow cytometry (e.g., by detecting CD-41 as a surface marker). Peptide probe labeled with FITC (PEP-11) stored in organic solvent is brought to room temperature. The organic solvent is removed by rotovaporation or air evaporation. The first sample is diluted in HEPES-buffered saline and subsequently combined with the peptide probe solution. The resulting combination is stored in the dark at room temperature for up to an hour, in order to allow the labeled peptide probe to bind to any Aβ oligomer associated with platelets present in the first sample.

A second sample containing PRP is obtained in the same manner as described above. The second sample is diluted in HEPES-buffered saline and subsequently combined with synthetic Aβ oligomer, and the synthetic Aβ oligomer is allowed to bind to any Aβ oligomer associated with platelets present in the second sample. Peptide probe labeled with FITC (PEP-11) stored in organic solvent is brought to room temperature. The organic solvent is removed by rotovaporation or air evaporation. The peptide probe is combined with the second sample and the resulting combination is stored in the dark at room temperature, allowing the labeled peptide probe to bind to any Aβ oligomer (endogenous and synthetic) associated with platelets present in the samples.

The first and second samples are subjected to a FACScan flow cytometer in TruCount Tubes to isolate platelets in the test samples. The platelets in the test samples are gated in logarithmic forward/side scatter dot plots, and the fluorescence of the FITC labels are detected by appropriate bandpass filters. In the first sample, complexes comprising labeled peptide probe-endogenous Aβ oligomer-platelets will be detected, while in the second sample complexes comprising labeled peptide probe-endogenous Aβ oligomer-platelets and complexes comprising labeled peptide probe-synthetic Aβ oligomer-platelets will be detected.

Example 4—Flow Cytometry on Cerebrospinal Fluid

Cerebrospinal fluid (CSF) is obtained from a subject by either lumbar puncture or from a previously separated frozen sample (clinical collection). Peptide probe labeled with FITC (PEP-11) stored in organic solvent is brought to room temperature. The organic solvent is removed by rotovaporation or air evaporation. The CSF is diluted in HEPES-buffered saline and combined with the peptide probe solution. The resulting combination is stored in the dark at room temperature for up to an hour, in order to allow the labeled peptide probe to bind to any Aβ oligomer present in the first test sample.

The sample is subjected to a FACScan flow cytometer in TruCount Tubes. Any Aβ oligomer in the test sample is gated in logarithmic forward/side scatter dot plots, and the fluorescence of the FITC labels are detected by appropriate bandpass filters. Complexes comprising labeled peptide probe and Aβ oligomer are detected.

Example 5—Peptide Linked Immunosorbent Assay (PLISA)

Figure 7:
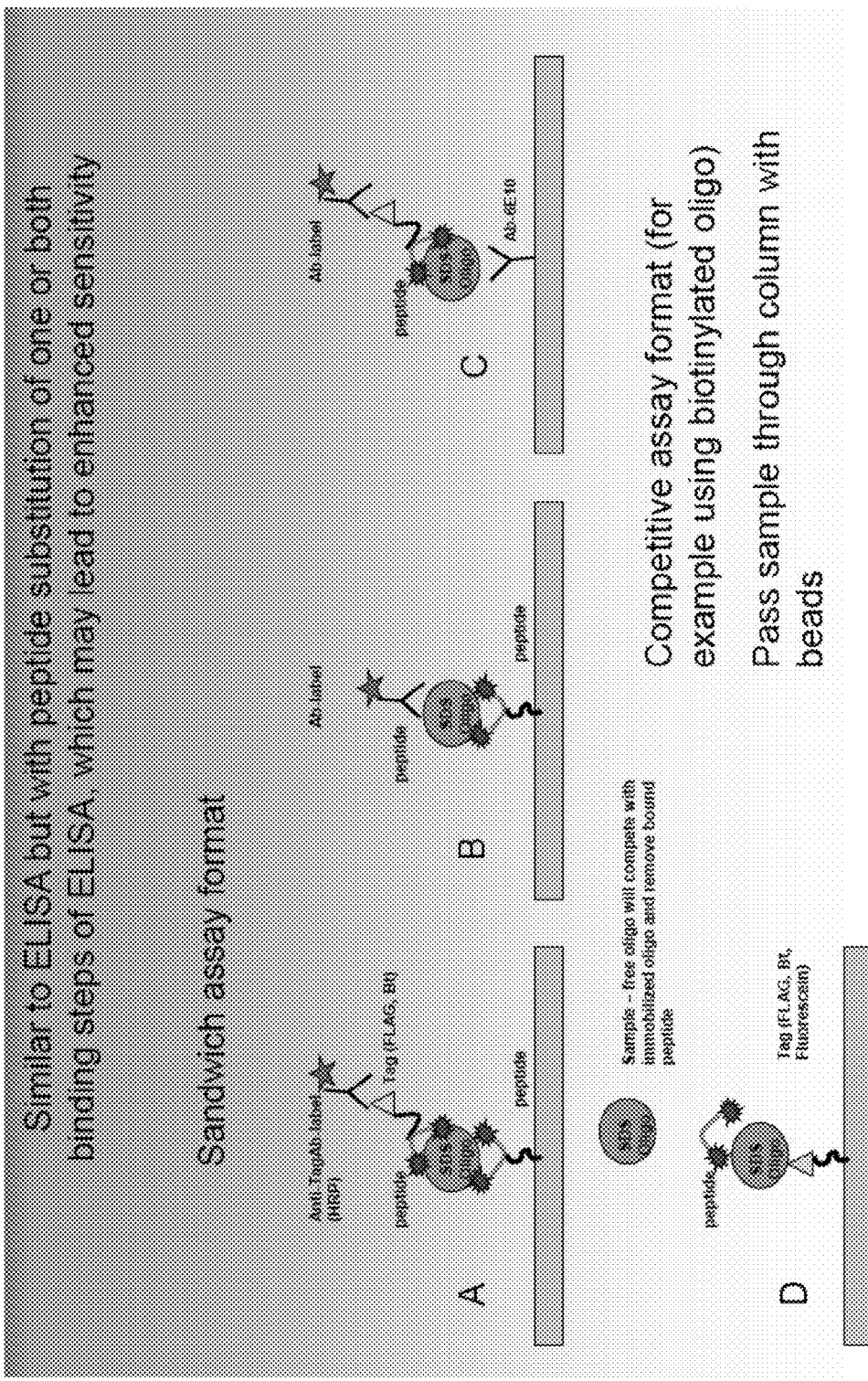
FIG. 7 depicts different formats for Peptide Linked Immunosorbent Assay (PLISA).

FIG. 7 depicts different formats for a PLISA as described herein. PLISA (A) depicts a sandwich format in which a target oligomer, such as an Aβ oligomer (SDS Oligo), binds to both surface-bound peptide probe (peptide) and peptide probe tagged with a label (Tag). The complex is detected using a labeled antibody (Anti-TagAb-label). PLISA (B) depicts a sandwich format in which the peptide probe tagged with a label is replaced by a labeled antibody (Ab-label) specific to the Aβ oligomer. PLISA (C) depicts a sandwich format in which the surface-bound peptide probe is replaced with an antibody specific to the Aβ oligomer (Ab-6E10). PLISA (D) depicts a competitive format in which Aβ oligomer in a biological sample competes with surface-bound Aβ oligomer for a labeled peptide probe. Each of PLISA (A)-(D) can use a solid-phase format (shown here as a bead, in which the bead is passed through an apparatus for detecting the labels).

Example 6—PLISA is More Sensitive and Selective Compared to ELISA

Figure 8:
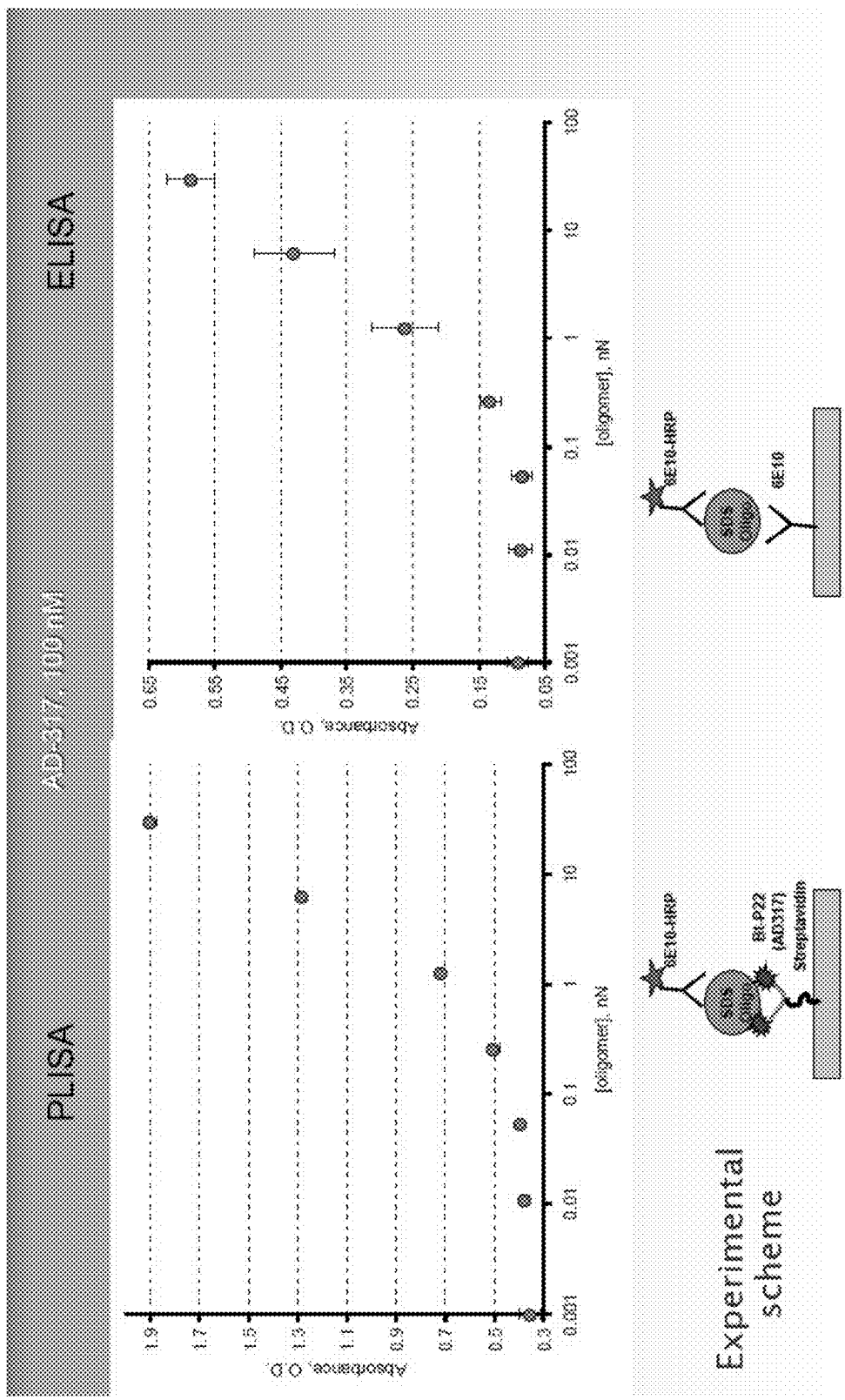
FIG. 8 depicts fluorescence values (O.D. absorbance) as a function of Aβ oligomer concentration for Peptide-Linked Immunosorbent Assay (PLISA) and Enzyme-Linked Immunosorbent Assay (ELISA), and demonstrates that peptide probes can be used to detect Aβ oligomer with greater sensitivity.

Different concentrations of Aβ oligomer in solution are subjected to both PLISA and ELISA to determine the sensitivity of each assay, as measured by dose response curves. For the PLISA assay, the peptide probe used is AD317 (SEQ ID NO:41). For the ELSIA, the antibody used is Aβ antibody 6E10 labeled with horse radish peroxidase. As shown in FIG. 8, the PLISA is a more sensitive assay for detecting Aβ oligomer than the ELISA.

Three different concentrations (nN) of Aβ oligomer, Aβ monomer, and Aβ fiber in solution were subjected to both PLISA and ELISA, either in buffer or 10% CSF, to determine the selectivity of each assay for Aβ oligomer as compared to the other Aβ forms. Tables 1 and 2 in FIG. 9 depict the results in buffer and 10% CSF, respectively, presented as a percent ratio of (monomer or fiber)/oligomer signal for the different oligomer concentrations. The data presented in both tables demonstrate a greater selectively of PLISA for Aβ oligomer over both Aβ monomer and Aβ fiber, as compared to ELISA.

Example 7—PLISA Using Pep-11 Distinguishes Aβ Oligomer from Monomer and Fiber

Different aggregate forms of Aβ protein (monomer, oligomer, and fiber) are subjected to PLISA using different PEP-11 peptide probe (Pep11-a, Pep11-b and Pep11-ds) and a control sample without PEP-11 peptide probe. Both Pep11-a and Pep11-b consist of SEQ ID NO:64, at a purity of 86% (standard) and 95% (high), respectively, as determined by high performance liquid chromatography (200 nm, C18, linear gradient). PEP-11ds is also represented by SEQ ID NO:64, but has a disulfide bridge at the two cysteines. High performance liquid chromatography (200 nm, C18, linear gradient) determined the purity of PEP-11ds to be 86.46%.

Figure 10:
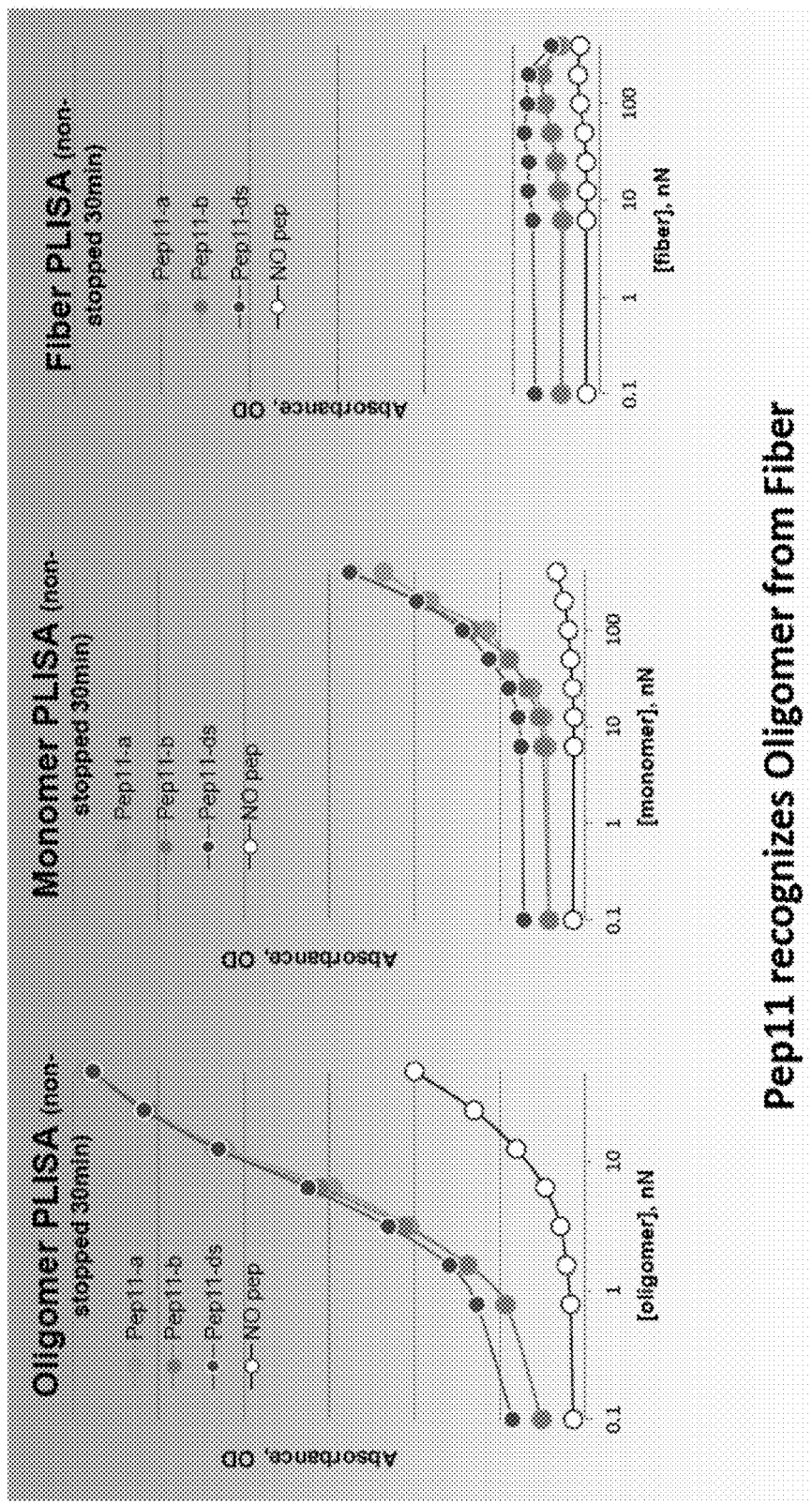
FIG. 10 depicts the ability of different peptide probes (Pep11-a, Pep11-b and Pep11-ds) to detect Aβ oligomer, Aβ monomer, or Aβ fiber by PLISA, and illustrates that the three peptide probes preferentially detect Aβ oligomer.

FIG. 10 demonstrates that all of the PEP-11 peptides detect Aβ oligomer in a dose-dependent manner, and exhibit preferential binding to Aβ oligomer as compared to Aβ monomer or fiber. These results demonstrate that the PEP-11 peptide probe preferentially binds to Aβ oligomer and can distinguish Aβ oligomer from other types of Aβ protein aggregates.

Example 8—Detection of Aβ Oligomer in Human CSF

Samples of CSF from a normal human subject are spiked with different concentrations of synthetic Aβ oligomer, and subjected to fluorescence detection assay using peptide probe AD315 (SEQ ID NO:65). The detection is performed in an assay with the following conditions: 10 mM HEPES buffer at pH 7.0; 0.005% NP-40; 10% normal human cerebrospinal fluid; 70 nM pyrenated peptide; and 37° C. incubation.

Figure 11:
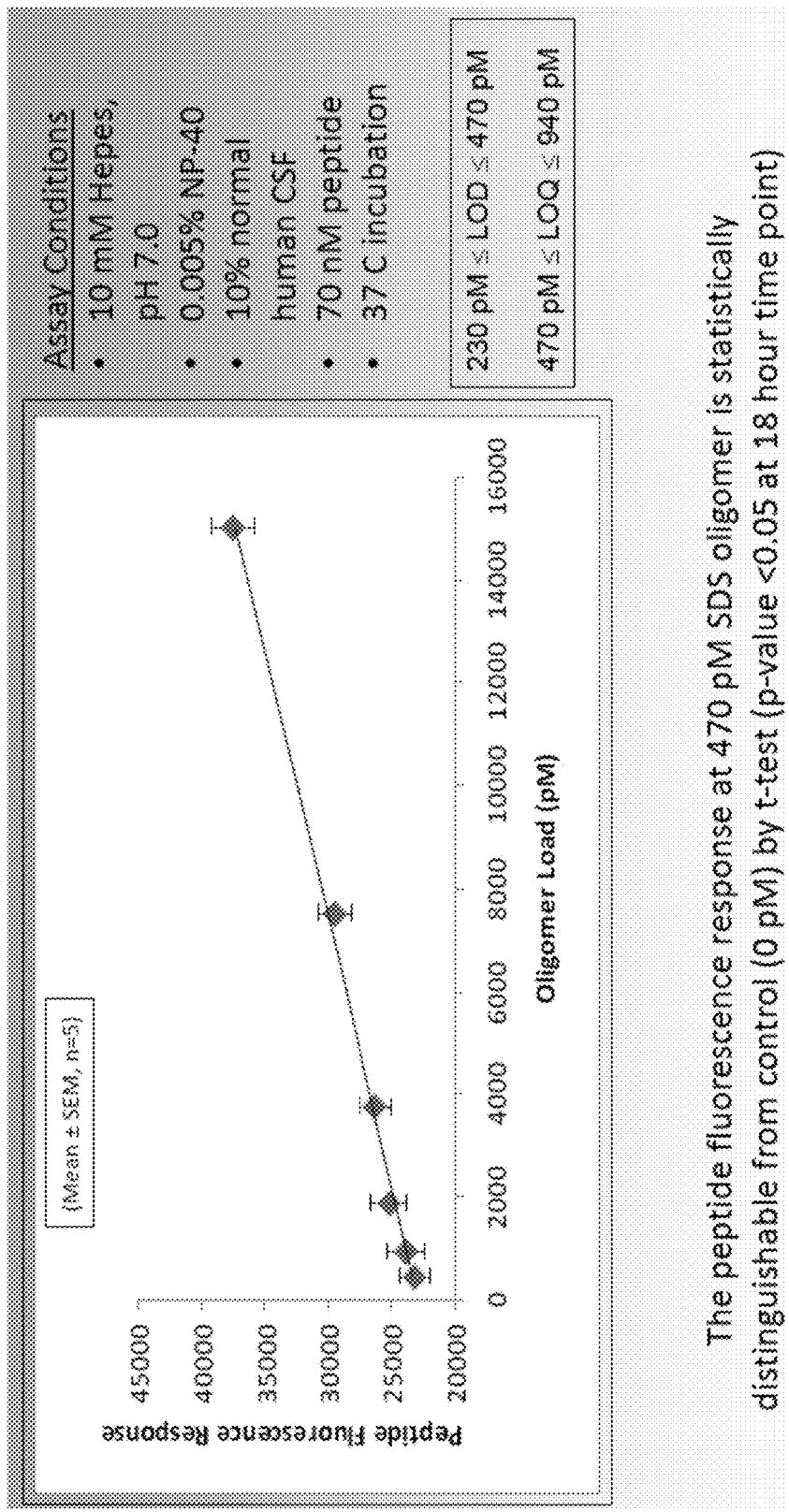
FIG. 11 depicts the ability of labeled peptide probe to detect synthetic Aβ oligomer in cerebrospinal fluid.

FIG. 11 depicts the results, which show a linear, dose-dependent curve. The results demonstrate that the assay can be used to detect Aβ oligomer in cerebrospinal fluid.

Example 9—Peptide Probe Binds Aβ42 Oligomer

Figure 12:
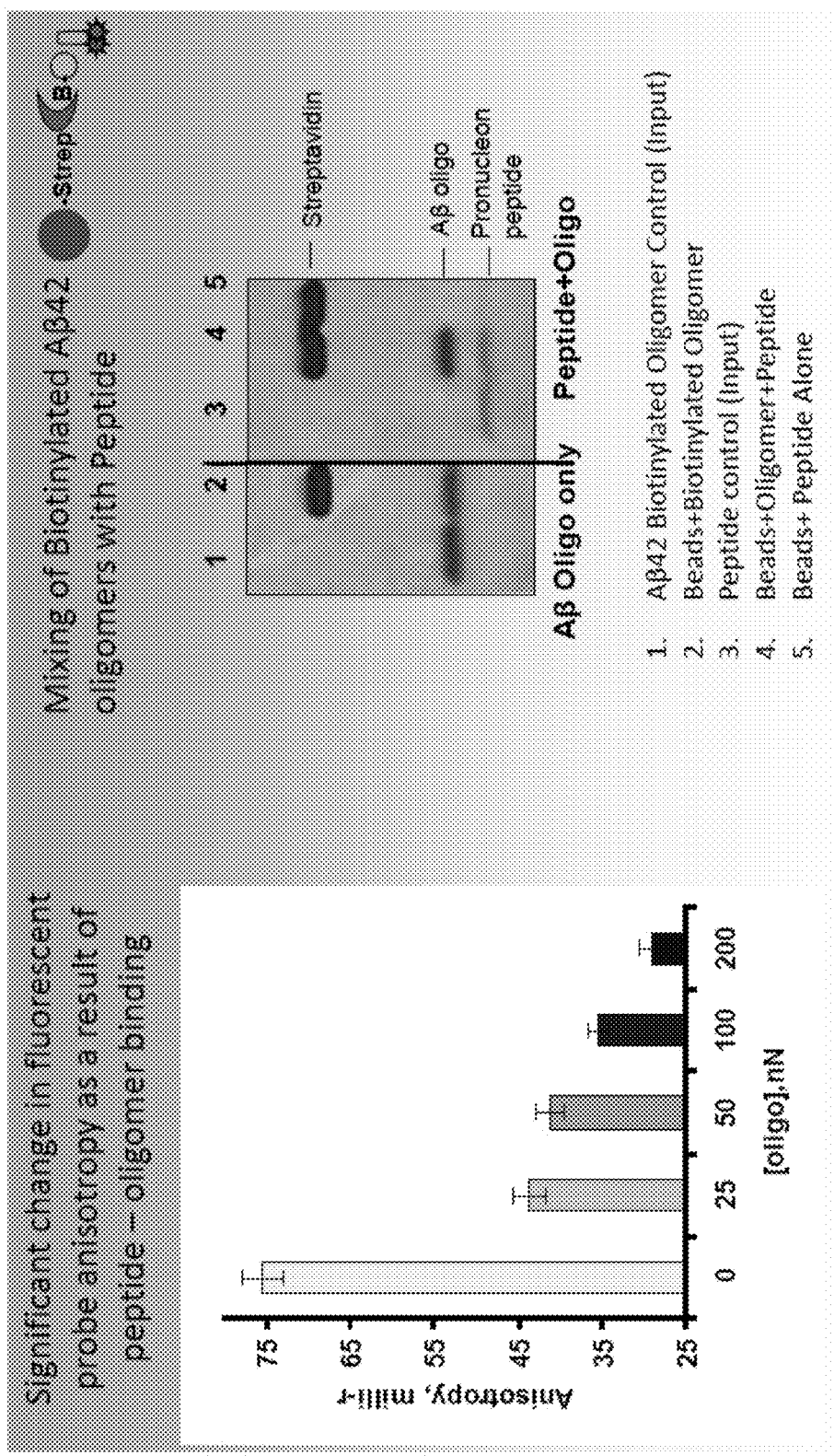
FIG. 12 depicts (i) gel electrophoresis bands depicting samples comprising (1) Aβ42 biotinylated oligomer; (2) Aβ42 biotinylated oligomer bound to beads via streptavidin; (3) peptide probe; (4) peptide probe bound to Aβ42 biotinylated oligomer bound to beads via streptavidin; and (5) peptide probe and streptavidin-coated beads. The figure also depicts (ii) fluorescent anisotropy (milli-r) as a function of Aβ42 oligomer concentration (nN). This information demonstrates that the peptide probes bind to Aβ oligomer with specificity and that the binding exhibits a dose-response profile.

An assay is performed to analyze peptide probe binding to Aβ42 oligomer. The peptide probe is the same as the probe in EXAMPLE 8. Five samples are analyzed: (1) Aβ42 biotinylated oligomer as a positive control; (2) Aβ42 biotinylated oligomer bound to a bead via streptavidin; (3) peptide positive control; (4) peptide probe bound to Aβ42 biotinylated oligomer bound to a bead via streptavidin; and (5) peptide probe bound to a bead via streptavidin. Detection was by gel electrophoresis. Results are shown in FIG. 12. As column 4 indicates by the presence of streptavidin, peptide probe can be used to detect Aβ42 oligomer.

FIG. 12 also shows a graph of fluorescent anisotropy (milli-r) as a function of Aβ42 oligomer concentration (nN). The peptide probe used to produce this data is the same as the peptide probe for the gel electrophoresis data above. Anisotropy decreases as oligomer concentration increases.

The results of the assay, as presented by FIG. 12, show that the peptide probes demonstrate specificity and sensitivity for the oligomeric form of Aβ protein.

Example 10—Clinical Study

Samples of human CSF from (1) subjects likely having Alzheimer's Disease (AD) (47 samples); (2) subjects having Mild Cognitive Impairment (MCI) (21 samples); and (3) normal subjects (i.e., not having AD or MCI) (32 samples) are subjected to an assay using pyrenated peptide. The purpose of the assay is to determine whether pyrenated peptide can accurately distinguish CSF samples based on the clinical condition of the subjects. The results of the assay are compared against results of commercially available ELISA kits that detect Aβ42 oligomer, total tau and phosphorylated-tau.

Figure 13:
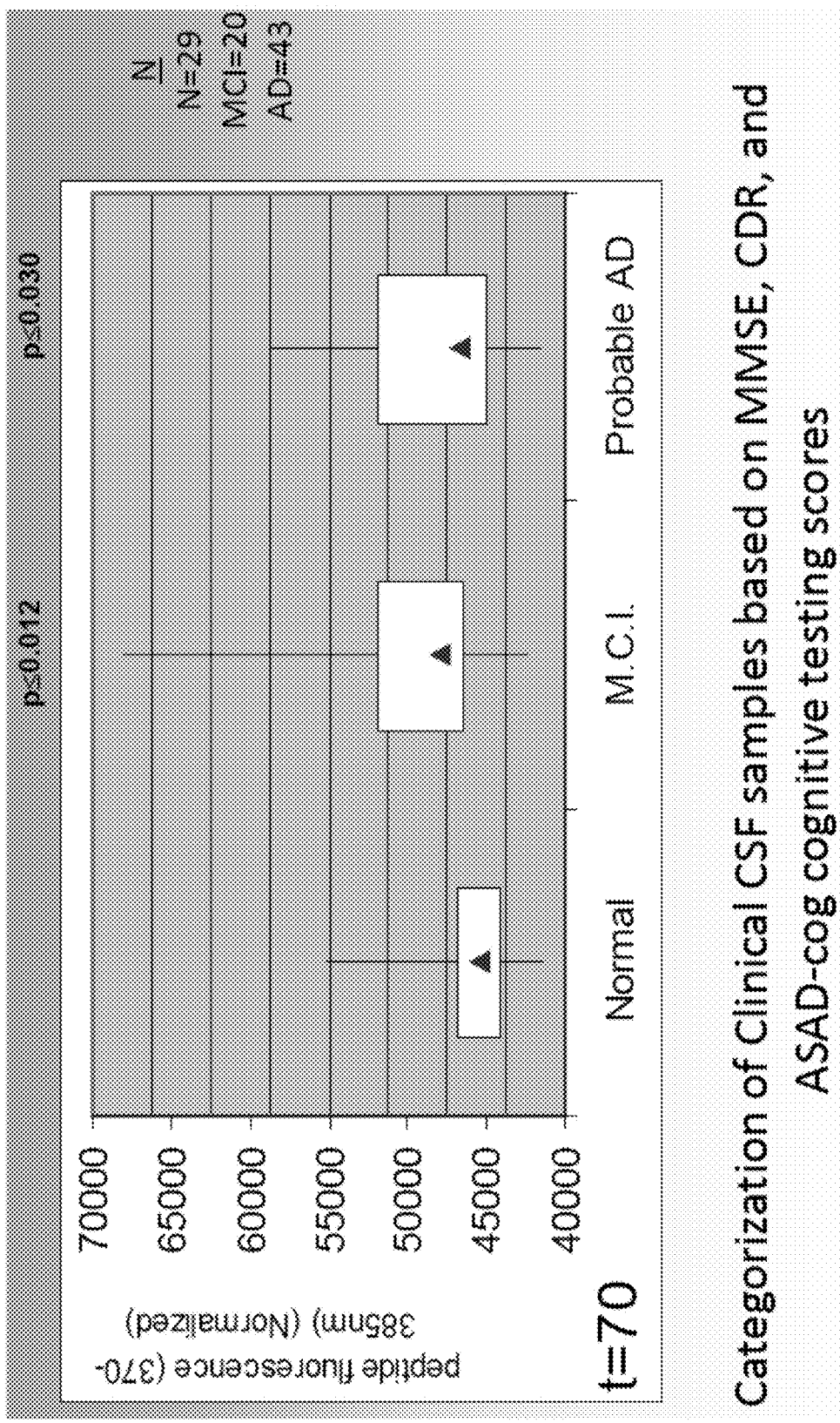
FIG. 13 depicts the ability of labeled peptide probe to distinguish between normal subjects and subjects having Mild Cognitive Impairment ($p \leq 0.012$) and between normal subjects and subjects suspected of having Alzheimer's Disease ($p \leq 0.030$), as determined by the peptide fluorescence of CSF samples probed with labeled peptide probe.

FIG. 13 demonstrates that peptide probe AD272 (SEQ ID NO: 22), can distinguish between MCI and normal subjects (p≤0.012) and between AD and normal subjects (p≤0.030) using fluorescence detection.

TABLE 1

| SEQ ID NO: | Category | Name | Modification | Sequence |
|---|---|---|---|---|
| 1 | Wildtype | WT | Aβ protein residues 16-35, with added C-Terminal Lys | KLVFF AEDVG SNKGA IIGLM K |
| 6 | Stability | AD250 | M35A to replace oxidizable methionine residue | KLVFF AEDVG SNKGA IIGLA K |
| 2 | Salt Bridge | P22 | Salt bridge at G29H and G33E, also induce alpha-helix, and increase solubility | KLVFF AEDVG SNKHA IIELM K |
| 65 | | AD315 | Salt bridge at G29H and G33E, also induce alpha-helix, and increase solubility; PBA and NH₂ additions | PBA-KLVFF AEDVG SNKHA IIELM K(PBA)-NH₂ |
| 14 | | P22 v.1 | Salt bridge at G29R and G33E | KLVFF AEDVG SNKRA IIELM K |
| 15 | | P22 v.2 | Salt bridge at G29K and G33E | KLVFF AEDVG SNKKA IIELM K |
| 3 | Salt Bridge + Alpha Helix | P38 | Salt bridge at G29H and G33E; Ala substitutions to increase alpha-helicity | KLVFF AEDAA AAKHA IIELM K |
| 4 | | P45 | Salt bridge at G29H and G33E; Ala additions to increase alpha-helicity | KAAA KLVFF AEDVG SNKHA IIELM K |
| 16 | Salt Bridge + Aβ Binding Motif | P77 | Salt bridge; Additional Aβ binding motif (GxxEG; SEQ ID NO: 25); extended N-terminus | HHQ KLVFF AEDEG SRKHA IEGLMEG K |
| 17 | | P59 | Salt bridge; Additional Aβ binding motif (GxxEG; SEQ ID NO: 25) | EAA KLVFF AEDEG SRKHA IEGLM EG K |
| 19 | Based on Naturally Occurring Mutants | Italian | P22, with E22K point mutation | KLVFF AKDVG SNKHA IIELM K |
| 20 | | Dutch | P22, with E22Q point mutation | KLVFF AQDVG SNKHA IIELM K |
| 21 | | Arctic | P22, with E22G point mutation | KLVFF AGDVG SNKHA IIELM K |
| 22 | Solubility | AD272 | WT, with 2 C-terminal dArg residues, and alternate label site | (PBA)KLVFF AEDVG SNKGA IIGLM K(PBA)rr |

TABLE 1-continued

| SEQ ID NO: | Category | Name | Modification | Sequence |
|---|---|---|---|---|
| 23 | | AD316 | P22, with 2 C-terminal dArg residues, and alternate label site | PBA-KLVFF AEDVG SNKHA IIELM K(PBA)rr |
| 24 | | AD305 | P22, with 2 N-terminal dArg residues, 2 C-terminal E residues and alternate label site | rrK(PBA)LVFF AEDVG SNKHA IIELM K(PBA)EE |
| 1 | | AD274 | WT, with PEG10 at C-terminus | (PBA)KLVFF AEDVG SNKGA IIGLM K(PBA)PEG10 |
| 26 | | AD271 | P45, with two dArg residues at C-terminus | (PBA)KAAA KLVFF AEDVG SNKHA IIELM K(PBA)rr |
| 27 | Induce Alpha-Helix + Solubility | AD273 | WT, with addition of Ala stretch (for alpha-helix formation) and dArg residues (for solubility) | (PBA)KAAA KLVFF AEDVG SNKGA IIGLM K(PBA)rr |
| 28 | Reduce Stability of B-sheet | AD323 | P22, with point mutations H29D and I31D | KLVFF AEDVG SNKDA DIELM K |
| 29 | | AD325 | P22, with point mutation S26D | KLVFF AEDVG DNKHA IIELM K |
| 30 | | AD330 | P22, with point mutation I31D | KLVFF AEDVG SNKHA DIELM K |
| 31 | | AD329 | P22, with point mutation L34D | KLVFF AEDVG SNKHA IIEDM K |
| 32 | | AD328 | P22, with point mutation H29D | KLVFF AEDVG SNKDA IIELM K |
| 33 | | AD327 | P22, with point mutation S26D, I31D | KLVFF AEDVG DNKHA DIELM K |
| 34 | | GM6 | P22, with point mutations F19S, L34P | KLVSF AEDVG SNKHA IIEPM K |
| 35 | | GM6 var. 1 | P22, with point mutation F19S | KLVSF AEDVG SNKHA IIELM K |
| 5, 18 | | I32S | Wildtype, with I32S point mutation | KLVFF AEDVG SNKGA ISGLM K |
| 36 | Label (PBA) Site | AD266 | WT, with label on side chain of N-terminal Lys | K(PBA)LVFF AEDVG SNKGA IIGLM K(PBA) |
| 37 | | AD268 | WT, with label on side chain of near N-terminal Lys; addition of solubilizing dArg and E residues | EK(PBA)LVFF AEDVG SNKGA IIGLM K(PBA)rrr |
| 38 | Biotin | AD310 | P22, biotin labeled with helical linker at C-terminus | (PBA)KLVFF AEDVG SNKHA IIELM K(PBA)EAAAK(biotin) |
| 39 | | AD313 | P22, biotin labeled at side chain of internal Lys | (PBA)KLVFF AEDVG SNK(biotin)HA IIELM K(PBA) |

TABLE 1-continued

| SEQ ID NO: | Category | Name | Modification | Sequence |
|---|---|---|---|---|
| 40 | | AD314 | P22, biotin labeled with flexible linker at C-terminus | (PBA)KLVFF AEDVG SNKHA IIELM K(PBA)GSSGSSK(biotin) |
| 41 | | AD317 | P22, biotin labeled with thrombin site linker, at C-terminus | (PBA)KLVFF AEDVG SNKHA IIELM K(PBA)GLVP RGSGK(biotin) |
| 42 | | AD321 | P22, biotin labeled with "kinked" linker at C-terminus | (PBA)KLVFF AEDVG SNKHA IIELM K(PBA)PSGSPK(biotin) |
| 2, 43 | Label/ Quencher Pairs | AD326 | P22, with pyrene and Dabcyl quencher | (PBA)KLVFF AEDVG SNKHA IIELM K(Dabcyl) |
| 44 | | AD309 | WT, with EDANS and Dabcyl quencher and solubilizing E residue | E(EDANS)LVFF AEDVG SNKGA IIGLM K(Dabcyl) |
| 45 | | AD306 | Wildtype Aβ residues 5-42, with EDANS and Dabcyl quencher and solubilizing E residue | E(EDANS)R HDSGY EVHHQ KLVFF AEDVG SNKGA IIGLM VGGVV IA K(Dabcyl) |
| 46 | | AD303 | Wildtype Aβ residues 3-35, with EDANS and Dabcyl quencher and solubilizing E residue | E(EDANS)EFR HDSGY EVHHQ KLVFF AEDVG SNKGA IIGLM K(Dabcyl) |
| 47 | | AD302 | P59, with EDANS and Dabcyl quencher and solubilizing E residue | E(EDANS)AAA KLVFF AEDEG SRKHA IEGLM EGK(Dabcyl) |
| 48 | | AD301 | P77, with EDANS and Dabcyl quencher and solubilizing E residue | E(EDANS)HHQ KLVFF AEDEG SRKHA IEGLM EGK(Dabcyl) |
| 49 | | AD300 | P22 with EDANS and Dabcyl quencher and solubilizing E residue | E(EDANS)LVFF AEDVG SNKHA IIELM K(Dabcyl) |
| 50 | FRET Pairs | AD295 | P22, with Dansyl and Trp | (Dansyl)KLVFF AEDVG SNKHA IIELM W |
| 51 | | AD294 | WT, with FAM and EDANS and solubilizing E residue | (FAM)KLVFF AEDVG SNKGA IIGLM E(EDANS) |
| 52 | | AD293 | P22, with FAM and EDANS and solubilizing E residue | (FAM)KLVFF AEDVG SNKHA IIELM E(EDANS) |
| 53 | | AD292 | Aβ residues 3-35, with FAM and EDANS and solubilizing E residue | (FAM)EFR HDSGY EVHHQ KLVFF AEDVG SNKGA IIGLM E(EDANS) |
| 54 | | AD291 | P77, with FAM and EDANS and solubilizing E residue | (FAM)HHQ KLVFF AEDEG SRKHA IEGLM EGE(EDANS) |

TABLE 1-continued

| SEQ ID NO: | Category | Name | Modification | Sequence |
|---|---|---|---|---|
| 55 | | AD290 | P59, with FAM and EDANS, additional Ala, and solubilizing E residue | (FAM)EAA KLVFF AEDEG SRKHA IEGLM EGE(EDANS) |
| 56 | | WT17-35 | Aβ protein residues 17-35, with added N- and C-Terminal Cys | CLVFF AEDVG SNKGA IIGLMC |
| 63 | | PEP-10 | WT17-35 with FITC label | FITC-Ahx-CLVFF AEDVG SNKGA IIGLMC-NH$_2$ |
| 64 | | PEP-11 | WT17-35 with FITC and d-Arginine at C-Terminal | FITC-Ahx-CLVFF AEDVG SNKGA IIGLMCrr-NH$_2$ |
| 62 | | PEP-12 | P-22 with FITC label, d-Arginine at C-Terminal and Histidine and Glutamic Acid substitutions | FITC-Ahx-CLVFF AEDVG SNKHA IEGLMCrr-NH$_2$ |

What is claimed is:

1. A method of determining the amyloid beta (Aβ) oligomer load of a subject by detecting Aβ oligomer associated with cells present in a biological sample obtained from the subject, comprising:
   preparing a first test sample comprising a biological sample from the subject that comprises cells and a peptide probe,
   wherein the peptide probe consists of from 10 to 34 amino acid residues comprising an amino acid sequence that is at least 70% identical to any one of SEQ ID NOs: 1-56 and 62-65, wherein the peptide probe preferentially binds to Aβ oligomers and is labeled with a detectable fluorescent label, wherein the peptide probe forms a first labeled complex with the Aβ oligomers on Aβ oligomer-associated cells in the biological sample;
   detecting a generated signal of the first labeled complex in the first test sample using flow cytometry;
   preparing a second test sample comprising a biological sample from the subject that comprises cells, synthetic Aβ oligomer, and the peptide probe, wherein the peptide probe forms second labeled complexes with Aβ oligomers on Aβ oligomer-associated cells in the biological sample and with synthetic Aβ oligomer;
   detecting a generated signal of the second labeled complexes in the second test sample using flow cytometry;
   wherein a difference between the signal of the first labeled complex in the first test sample and the signal of the second labeled complexes in the second test sample is inversely correlated with the Aβ oligomer load of the subject.

2. The method according to claim 1, wherein the second test sample is prepared by combining the biological sample and synthetic Aβ oligomer, and subsequently introducing the peptide probe.

3. The method according claim 1, wherein the peptide probe consists of SEQ ID NO:64 (Pep-11).

4. The method according to claim 1, wherein the fluorescent label is a fluorescein isothiocyanate (FITC) label.

5. The method according to claim 1, wherein the biological sample comprises a sample of body fluid.

6. The method according to claim 5, wherein the body fluid is selected from the group consisting of blood, blood plasma, cerebrospinal fluid (CSF), and brain homogenate.

7. The method according to claim 5, wherein the body fluid comprises Aβ oligomer-associated erythrocytes.

8. The method according to claim 7, wherein the erythrocytes are isolated erythrocytes.

9. The method according to claim 5, wherein the body fluid comprises Aβ oligomer-associated platelets.

10. The method according to claim 9, wherein the platelets are isolated platelets.

11. The method according to claim 2, wherein the biological sample comprises Aβ oligomer-associated cells selected from erythrocytes, platelets, leukocytes and tissue cells.

12. The method according to claim 11, wherein the biological sample comprises Aβ oligomer-associated erythrocytes and Aβ oligomer-associated platelets and the detecting comprises separately detecting Aβ oligomers associated with erythrocytes and Aβ oligomers associated with platelets.

13. The method according to claim 1, wherein the labeled complex formed and/or detected is selected from a labeled complex comprising peptide probe and Aβ oligomer on Aβ oligomer-associated erythrocytes from the biological sample; a labeled complex comprising peptide probe and Aβ oligomer on Aβ oligomer-associated platelets from the biological sample; and a labeled complex comprising peptide probe and synthetic Aβ oligomer on synthetic Aβ oligomer-associated erythrocytes or on synthetic Aβ oligomer-associated platelets from the biological sample.

14. An in vitro method of detecting amyloid beta (Aβ) oligomer associated with erythrocytes or platelets, comprising:
   contacting erythrocytes or platelets with a peptide probe, wherein the peptide probe consists of from 10 to 34 amino acid residues comprising an amino acid sequence that is at least 70% identical to any one of SEQ ID NOs: 1-56 and 62-65, wherein the peptide probe preferentially binds to Aβ oligomers and is labeled with a detectable label, wherein the peptide probe forms a labeled complex with the Aβ oligomers on Aβ oligomer-associated erythrocytes or Aβ oligomer-associated platelets; and
   detecting a generated signal of the labeled complex using flow cytometry.

\* \* \* \* \*

SEQUENCE LISTING

<160> NUMBER OF SEQ ID NOS: 65

<210> SEQ ID NO 1
<211> LENGTH: 21
<212> TYPE: PRT
<213> ORGANISM: Unknown
<220> FEATURE:
<223> OTHER INFORMATION: Description of Unknown:
      Amyloid-beta peptide

<400> SEQUENCE: 1

Lys Leu Val Phe Phe Ala Glu Asp Val Gly Ser Asn Lys Gly Ala Ile
1               5                   10                  15

Ile Gly Leu Met Lys
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Leu Val Phe Phe Ala Glu Asp Val Gly Ser Asn Lys His Ala Ile
1               5                   10                  15

Ile Glu Leu Met Lys
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 3

Lys Leu Val Phe Phe Ala Glu Asp Ala Ala Ala Lys His Ala Ile
1               5                   10                  15

Ile Glu Leu Met Lys
            20

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ala Ala Lys Leu Val Phe Phe Ala Glu Asp Val Gly Ser Asn
1               5                   10                  15

Lys His Ala Ile Ile Glu Leu Met Lys
            20                  25

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Val Phe Phe Ala Glu Asp Val Gly Ser Asn Lys Gly Ala Ile
1               5                   10                  15

Ser Gly Leu Met Lys
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Leu Val Phe Phe Ala Glu Asp Val Gly Ser Asn Lys Gly Ala Ile
1               5                   10                  15

Ile Gly Leu Ala Lys
            20

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000
```

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Leu Val Phe Phe Ala Glu Asp Val Gly Ser Asn Lys Arg Ala Ile
1               5                   10                  15

Ile Glu Leu Met Lys
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Val Phe Phe Ala Glu Asp Val Gly Ser Asn Lys Lys Ala Ile
1               5                   10                  15

Ile Glu Leu Met Lys
            20

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His His Gln Lys Leu Val Phe Phe Ala Glu Asp Glu Gly Ser Arg Lys
1               5                   10                  15

His Ala Ile Glu Gly Leu Met Glu Gly Lys
            20                  25

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Ala Ala Lys Leu Val Phe Phe Ala Glu Asp Glu Gly Ser Arg Lys
1               5                   10                  15

His Ala Ile Glu Gly Leu Met Glu Gly Lys
            20                  25

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Leu Val Phe Phe Ala Glu Asp Val Gly Ser Asn Lys Gly Ala Ile
1               5                   10                  15

Ser Gly Leu Met Lys
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Leu Val Phe Phe Ala Lys Asp Val Gly Ser Asn Lys His Ala Ile
1               5                   10                  15

Ile Glu Leu Met Lys
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Leu Val Phe Phe Ala Gln Asp Val Gly Ser Asn Lys His Ala Ile
1               5                   10                  15

Ile Glu Leu Met Lys
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Lys Leu Val Phe Phe Ala Gly Asp Val Gly Ser Asn Lys His Ala Ile
1               5                   10                  15

Ile Glu Leu Met Lys
                20
```

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(23)
<223> OTHER INFORMATION: D-Arg

<400> SEQUENCE: 22

```
Lys Leu Val Phe Phe Ala Glu Asp Val Gly Ser Asn Lys Gly Ala Ile
1               5                   10                  15

Ile Gly Leu Met Lys Arg Arg
                20
```

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(23)
<223> OTHER INFORMATION: D-Arg

<400> SEQUENCE: 23

```
Lys Leu Val Phe Phe Ala Glu Asp Val Gly Ser Asn Lys His Ala Ile
1               5                   10                  15

Ile Glu Leu Met Lys Arg Arg
                20
```

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-Arg

<400> SEQUENCE: 24

```
Arg Arg Lys Leu Val Phe Phe Ala Glu Asp Val Gly Ser Asn Lys His
1               5                   10                  15

Ala Ile Ile Glu Leu Met Lys Glu Glu
                20                  25
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (2)..(3)
<223> OTHER INFORMATION: Any amino acid

<400> SEQUENCE: 25

Gly Xaa Xaa Glu Gly
1               5

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(27)
<223> OTHER INFORMATION: D-Arg

<400> SEQUENCE: 26

Lys Ala Ala Ala Lys Leu Val Phe Phe Ala Glu Asp Val Gly Ser Asn
1               5                   10                  15
Lys His Ala Ile Ile Glu Leu Met Lys Arg Arg
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(27)
<223> OTHER INFORMATION: D-Arg

<400> SEQUENCE: 27

Lys Ala Ala Ala Lys Leu Val Phe Phe Ala Glu Asp Val Gly Ser Asn
1               5                   10                  15
Lys Gly Ala Ile Ile Gly Leu Met Lys Arg Arg
            20                  25

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Leu Val Phe Phe Ala Glu Asp Val Gly Ser Asn Lys Asp Ala Asp
1               5                   10                  15
Ile Glu Leu Met Lys
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

Lys Leu Val Phe Phe Ala Glu Asp Val Gly Asp Asn Lys His Ala Ile
1               5                   10                  15

Ile Glu Leu Met Lys
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Leu Val Phe Phe Ala Glu Asp Val Gly Ser Asn Lys His Ala Asp
1               5                   10                  15

Ile Glu Leu Met Lys
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Leu Val Phe Phe Ala Glu Asp Val Gly Ser Asn Lys His Ala Ile
1               5                   10                  15

Ile Glu Asp Met Lys
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Leu Val Phe Phe Ala Glu Asp Val Gly Ser Asn Lys Asp Ala Ile
1               5                   10                  15

Ile Glu Leu Met Lys
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Leu Val Phe Phe Ala Glu Asp Val Gly Asp Asn Lys His Ala Asp
1               5                   10                  15

Ile Glu Leu Met Lys
            20

<210> SEQ ID NO 34
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 34

Lys Leu Val Ser Phe Ala Glu Asp Val Gly Ser Asn Lys His Ala Ile
1               5                   10                  15

Ile Glu Pro Met Lys
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Leu Val Ser Phe Ala Glu Asp Val Gly Ser Asn Lys His Ala Ile
1               5                   10                  15

Ile Glu Leu Met Lys
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Leu Val Phe Phe Ala Glu Asp Val Gly Ser Asn Lys Gly Ala Ile
1               5                   10                  15

Ile Gly Leu Met Lys
            20

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(25)
<223> OTHER INFORMATION: D-Arg

<400> SEQUENCE: 37

Glu Lys Leu Val Phe Phe Ala Glu Asp Val Gly Ser Asn Lys Gly Ala
1               5                   10                  15

Ile Ile Gly Leu Met Lys Arg Arg Arg
            20                  25

<210> SEQ ID NO 38
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Leu Val Phe Phe Ala Glu Asp Val Gly Ser Asn Lys His Ala Ile
```

```
Ile Glu Leu Met Lys Glu Ala Ala Ala Lys
        20                  25

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Leu Val Phe Phe Ala Glu Asp Val Gly Ser Asn Lys His Ala Ile
1               5                   10                  15

Ile Glu Leu Met Lys
        20

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Leu Val Phe Phe Ala Glu Asp Val Gly Ser Asn Lys His Ala Ile
1               5                   10                  15

Ile Glu Leu Met Lys Gly Ser Ser Gly Ser Ser Lys
        20                  25

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Lys Leu Val Phe Phe Ala Glu Asp Val Gly Ser Asn Lys His Ala Ile
1               5                   10                  15

Ile Glu Leu Met Lys Gly Leu Val Pro Arg Gly Ser Gly Lys
        20                  25                  30

<210> SEQ ID NO 42
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Leu Val Phe Phe Ala Glu Asp Val Gly Ser Asn Lys His Ala Ile
1               5                   10                  15

Ile Glu Leu Met Lys Pro Ser Gly Ser Pro Lys
        20                  25

<210> SEQ ID NO 43
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 43

Lys Leu Val Phe Phe Ala Glu Asp Val Gly Ser Asn Lys His Ala Ile
1               5                   10                  15

Ile Glu Leu Met Lys
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Leu Val Phe Phe Ala Glu Asp Val Gly Ser Asn Lys Gly Ala Ile
1               5                   10                  15

Ile Gly Leu Met Lys
            20

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Arg His Asp Ser Gly Tyr Glu Val His His Gln Lys Leu Val Phe
1               5                   10                  15

Phe Ala Glu Asp Val Gly Ser Asn Lys Gly Ala Ile Ile Gly Leu Met
            20                  25                  30

Val Gly Gly Val Val Ile Ala Lys
        35                  40

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Glu Phe Arg His Asp Ser Gly Tyr Glu Val His His Gln Lys Leu
1               5                   10                  15

Val Phe Phe Ala Glu Asp Val Gly Ser Asn Lys Gly Ala Ile Ile Gly
            20                  25                  30

Leu Met Lys
        35

<210> SEQ ID NO 47
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

Glu Ala Ala Ala Lys Leu Val Phe Phe Ala Glu Asp Glu Gly Ser Arg
1               5                   10                  15

Lys His Ala Ile Glu Gly Leu Met Gly Lys
            20                  25

<210> SEQ ID NO 48
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu His His Gln Lys Leu Val Phe Phe Ala Glu Asp Glu Gly Ser Arg
1               5                   10                  15

Lys His Ala Ile Glu Gly Leu Met Gly Lys
            20                  25

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Leu Val Phe Phe Ala Glu Asp Val Gly Ser Asn Lys His Ala Ile
1               5                   10                  15

Ile Glu Leu Met Lys
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Leu Val Phe Phe Ala Glu Asp Val Gly Ser Asn Lys His Ala Ile
1               5                   10                  15

Ile Glu Leu Met Trp
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Leu Val Phe Phe Ala Glu Asp Val Gly Ser Asn Lys Gly Ala Ile
1               5                   10                  15

Ile Gly Leu Met Glu
            20

<210> SEQ ID NO 52
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 52

Lys Leu Val Phe Phe Ala Glu Asp Val Gly Ser Asn Lys His Ala Ile
1               5                   10                  15

Ile Glu Leu Met Glu
            20

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Glu

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His His Gln Lys Leu Val Phe Phe Ala Glu Asp Gly Ser Arg Lys
1               5                   10                  15

His Ala Ile Glu Gly Leu Met Glu Gly Glu
            20                  25

<210> SEQ ID NO 55
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Ala Ala Lys Leu Val Phe Phe Ala Glu Asp Glu Gly Ser Arg Lys
1               5                   10                  15

His Ala Ile Glu Gly Leu Met Glu Gly Glu
            20                  25

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Leu Val Phe Phe Ala Glu Asp Val Gly Ser Asn Lys Gly Ala Ile
1               5                   10                  15
```

Ile Gly Leu Met Cys
            20

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Ala Ala Ala Lys
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser Ser Gly Ser Ser Lys
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Val Pro Arg Gly Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Val Pro Arg Gly Ser Gly Lys
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Ser Gly Ser Pro Lys
1               5

<210> SEQ ID NO 62
<211> LENGTH: 24
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (23)..(24)
<223> OTHER INFORMATION: D-Arg

<400> SEQUENCE: 62

Xaa Cys Leu Val Phe Phe Ala Glu Asp Val Gly Ser Asn Lys His Ala
1               5                   10                  15

Ile Ile Glu Leu Met Cys Arg Arg
            20

<210> SEQ ID NO 63
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 63

Xaa Cys Leu Val Phe Phe Ala Glu Asp Val Gly Ser Asn Lys Gly Ala
1               5                   10                  15

Ile Ile Gly Leu Met Cys
            20

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (23)..(24)
<223> OTHER INFORMATION: D-Arg

<400> SEQUENCE: 64

Xaa Cys Leu Val Phe Phe Ala Glu Asp Val Gly Ser Asn Lys Gly Ala
1               5                   10                  15

Ile Ile Gly Leu Met Cys Arg Arg
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Leu Val Phe Phe Ala Glu Asp Val Gly Ser Asn Lys His Ala Ile
1               5                   10                  15

```
Ile Glu Leu Met Lys
            20
```